(12) United States Patent
Bae et al.

(10) Patent No.: US 11,878,013 B2
(45) Date of Patent: Jan. 23, 2024

(54) ISOQUINOLINE DERIVATIVE, PREPARING METHOD THEREOF, AND PHARMACEUTICAL COMPOSITION FOR PREVENTING OR TREATING AUTOPHAGY RELATED DISEASES CONTAINING THE SAME AS AN ACTIVE INGREDIENT

(71) Applicant: Korea Research Institute of Chemical Technology, Daejeon (KR)

(72) Inventors: Myung-Ae Bae, Daejeon (KR); Dae-Seop Shin, Daejeon (KR); Jung Yoon Yang, Daejeon (KR); Kyu Seok Hwang, Daejeon (KR); Seong Soon Kim, Daejeon (KR); Byung Hoi Lee, Daejeon (KR); Ki Young Kim, Daejeon (KR); Won Hoon Jung, Daejeon (KR); Jae Chun Woo, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 69 days.

(21) Appl. No.: 17/367,254

(22) Filed: Jul. 2, 2021

(65) Prior Publication Data
US 2023/0025531 A1    Jan. 26, 2023

(51) Int. Cl.
| | |
|---|---|
| A61K 31/472 | (2006.01) |
| A61K 31/47 | (2006.01) |
| A61K 9/00 | (2006.01) |
| A61P 1/16 | (2006.01) |
| A61P 29/00 | (2006.01) |
| A61P 17/00 | (2006.01) |

(52) U.S. Cl.
CPC .......... *A61K 31/472* (2013.01); *A61K 9/0014* (2013.01); *A61K 31/47* (2013.01); *A61P 1/16* (2018.01); *A61P 17/00* (2018.01); *A61P 29/00* (2018.01)

(58) Field of Classification Search
None
See application file for complete search history.

(56) References Cited

U.S. PATENT DOCUMENTS

| 5,145,843 A | 9/1992 | Arnold et al. | |
|---|---|---|---|
| 5,240,940 A | * 8/1993 | Arnold ................... | A01N 43/54 514/525 |

FOREIGN PATENT DOCUMENTS

| EP | 2 383 294 | 2/2011 |
|---|---|---|
| KR | 2020-0083134 | 7/2020 |
| WO | WO 1997/030035 | 8/1997 |

OTHER PUBLICATIONS

Mitsuoka et al. BMC Ophthalmology 2021 21:224:1-7 (Year: 2021).*
Das et al. International Journal of Molecular Sciences 2022 23:3111:1-21 (Year: 2022).*
West et al. Journal of Immunology 2014 192:1762-1767 (Year: 2014).*
Tummanapalli et al. The Ocular Surface 2021 21:37-51 (Year: 2021).*
Speeckaert et al. Pigment Cell Melanoma Research 2014 27:512-524 (Year: 2014).*
Wong et al. Journal of Cutaneous Medicine and Surgery 2021 25(1):77-86 (Year: 2021).*
Salgueiro et al. (2014) "Direct synthesis of 4-organylsulfenyl-7-chloro quinolines and their toxicological and pharmacological activities in Caenorhabditis elegans," European Journal of Medicinal Chemistry 75: 448-459.
Anczkiewicz et al. (2015) "Synthesis of 4-(4-toluenesulfonyl)quinolines from nitroarenes and allyl sulfones using step-by-step procedure," Tetrahedron 71: 3924-3931.
Xie et al. (2018) "Waste-Minimized Protocol for the Synthesis of Sulfonylated N-Heteroaromatics in Water," ACS Sustainable Chemistry & Engineering 6: 16976-16981.
Zhang et al. (2018) "Preparation of fluoroalkoxy or fluorophenoxy substituted N-heterocycles from heterocyclic N-oxides and polyfluoroalcohols," Organic Chemistry Frontiers: 2340-2344.
Kim et al. (2019) "Anti-inflammatory effect of a novel synthetic compound 1-((4-fluorophenyl)thio)isoquinoline in RAW264.7 macrophages and a zebrafish model," Fish and Shellfish Immunology 87: 395-400.
Ahn et al. (2020) "Identification of new arylsulfide derivatives as anti-melanogenic agents in a zebrafish model," Bioorganic & Medicinal Chemistry Letters 30 127201: 6 pages.

* cited by examiner

*Primary Examiner* — Melissa S Mercier
*Assistant Examiner* — Caralynne E Helm
(74) *Attorney, Agent, or Firm* — Leydig, Voit & Mayer, Ltd.

(57) ABSTRACT

The present invention relates to a novel isoquinoline derivative, a preparing method thereof, and a pharmaceutical composition for preventing or treating autophagy related diseases containing the same as an active ingredient. The novel isoquinoline furanone derivative according to the present invention is capable of regulating autophagy activity, and thus, by using this derivative as an active ingredient, there is a useful effect that can be used as a pharmaceutical composition for preventing or treating autophagy-related diseases such as neurodegenerative diseases, cancer, metabolic diseases, inflammatory diseases or melanogenesis-related diseases, a health functional food composition for ameliorating thereof, or a cosmetic composition with a whitening function.

9 Claims, 11 Drawing Sheets

ISOQUINOLINE DERIVATIVE, PREPARING METHOD THEREOF, AND PHARMACEUTICAL COMPOSITION FOR PREVENTING OR TREATING AUTOPHAGY RELATED DISEASES CONTAINING THE SAME AS AN ACTIVE INGREDIENT

BACKGROUND OF THE INVENTION

1. Field of the Invention

The present invention relates to a novel isoquinoline derivative, a preparing method thereof, and a pharmaceutical composition for preventing or treating autophagy related diseases containing the same as an active ingredient.

2. Description of the Related Art

Autophagy plays an important role in regulating cellular functions such as survival under starvation, protection from infectious bacteria, and regulation of neuronal decay. Autophagy is an evolutionarily conserved process and is known to be observed in all eukaryotic cells from yeast to mammals.

When autophagy is activated, an autophagosome membrane structure is formed by the atg12-atg5 complex and LC3 aggregation. The cytosolic form of LC3 (LC3-I) is split into the membrane-bound form (LC3-II), and the membrane matures into autophagosome surrounding the component to be degraded. Then, the autophagosome fuses with lysosome to form autolysosome, which causes lysosomal degradation of intracellular components. Various studies are currently underway to elucidate the complicated molecular mechanisms involved in this process.

Meanwhile, autophagy is associated with various pathological processes such as neurodegenerative diseases, cancer, and melanogenesis. In cancer, autophagy can be associated with various stages, where oxygen and nutrients are limited in growing tumor cells, so autophagy is used for survival until the necessary components are provided by angiogenesis. In this case, autophagy must be inhibited to stop tumor cell survival.

Melanogenesis refers to the formation of melanin, a pigment found in the eyes, skin and hair. Increased autophagosomes are observed in pigmentary disorder patients, and more recent studies have reported that lack of beclin 1 or LC3-I significantly attenuates pigment accumulation. In an in vivo assay, lack of beclin 1 heterozygosity resulted in mouse coat pigmentation defects. Melanogenesis is activated by stimulation of external factors such as UV. Pigmentary disorders (melasma, freckles, age spots, etc.) can be caused by melanogenesis. In this case, autophagy must be inhibited to stop melanin hyperproduction.

As described above, in autophagy-related neurodegenerative diseases, cancer and melanin hyperproduction, it is possible to develop a drug capable of regulating autophagy as a potential drug candidate.

On the other hand, as a Beclin 1 related patent involved in autophagy mechanism, EP 2383294 discloses techniques for treating or diagnosing neurodegenerative diseases using antibodies specific for Beclin 1 phosphorylated at position Thr 119.

Ahn et al. reported that 1-((4-fluorophenyl)thio)isoquinoline exhibits an anti-melanogenic effect (Bioorganic & Medicinal Chemistry Letters 30 (2020) 127201).

SUMMARY OF THE INVENTION

It is an object of the present invention to provide a novel isoquinoline derivative as an active ingredient for providing a drug for regulating autophagy activity.

It is another object of the present invention to provide a method for preparing the isoquinoline derivative.

It is another object of the present invention to provide a pharmaceutical composition for preventing or treating autophagy related diseases containing the isoquinoline derivative as an active ingredient.

It is another object of the present invention to provide a pharmaceutical composition for preventing or treating inflammatory or metabolic diseases containing the isoquinoline derivative as an active ingredient.

It is another object of the present invention to provide a pharmaceutical composition for preventing or treating skin hyperpigmentation disease containing the isoquinoline derivative as an active ingredient.

To achieve the above objects, in an aspect of the present invention, the present invention provides a compound represented by formula 1 or a pharmaceutically acceptable salt thereof.

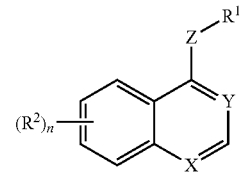

[Formula 1]

(In formula 1,
$R^1$ is nonsubstituted or substituted phenyl,
wherein the substituted phenyl is substituted with one or more substituents selected from the group consisting of hydroxy, cyano, nitro, amino, halogen, and nonsubstituted or substituted straight or branched $C_{1-5}$ alkyl,
wherein the substituted alkyl is substituted with halogen;
$R^2$ is hydroxy, amino, cyano, halogen, $C_{1-3}$ straight or branched alkyl, or $C_{1-3}$ straight or branched alkoxy;
n is an integer of 0~8;
X and Y are independently CH or N; and
Z is sulfinyl or sulfonyl).

In another aspect of the present invention, the present invention provides a preparation method of a compound represented by formula 1 comprising a step of preparing a compound represented by formula 1 from a compound represented by formula 4; as shown in reaction formula 1 below:

[Reaction Formula 1]

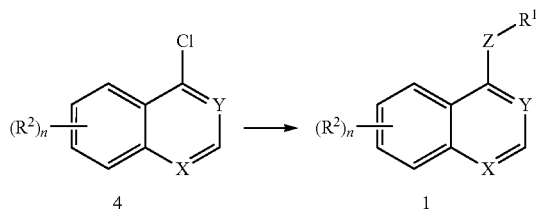

(In reaction formula 1,
$R^1$, $R^2$, n, X, Y and Z are as defined in formula 1 above).

In another aspect of the present invention, the present invention provides a pharmaceutical composition for preventing or treating autophagy related diseases containing a compound represented by formula 1 or a pharmaceutically acceptable salt thereof as an active ingredient.

In another aspect of the present invention, the present invention provides a pharmaceutical composition for preventing or treating inflammatory or metabolic diseases containing a compound represented by formula 1 or a pharmaceutically acceptable salt thereof as an active ingredient.

In addition, in another aspect of the present invention, the present invention provides a pharmaceutical composition for preventing or treating skin hyperpigmentation disease containing a compound represented by formula 1 or a pharmaceutically acceptable salt thereof as an active ingredient.

Advantageous Effect

The novel isoquinoline furanone derivative according to the present invention is capable of regulating autophagy activity, and thus, by using this derivative as an active ingredient, there is a useful effect that can be used as a pharmaceutical composition for preventing or treating autophagy-related diseases such as neurodegenerative diseases, cancer, metabolic diseases, inflammatory diseases or melanogenesis-related diseases, a health functional food composition for ameliorating thereof, or a cosmetic composition with a whitening function.

DETAILED DESCRIPTION OF THE INVENTION

Figure 1:
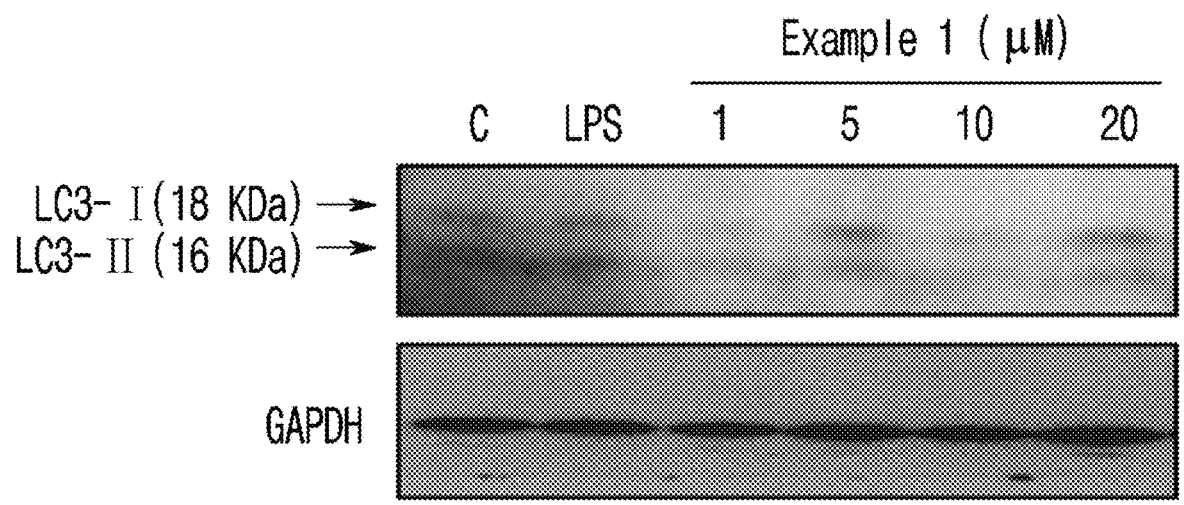
FIG. 1 is a set of Western blot diagrams confirming the conversions of LC3-I and LC3-II according to the treatment of the compound of Example 1 of the present invention at the concentrations of 1, 5, 10, and 20 μM in Raw 264.7 mouse macrophages.

Hereinafter, the present invention is described in detail.

The following description is provided to help the understanding of the present invention, and the present invention is not limited to the content of the following description.

In an aspect of the present invention, the present invention provides a compound represented by formula 1 or a pharmaceutically acceptable salt thereof.

[Formula 1]

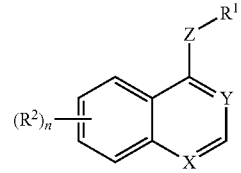

(In formula 1, $R^1$ is nonsubstituted or substituted phenyl, wherein the substituted phenyl is substituted with one or more substituents selected from the group consisting of hydroxy, cyano, nitro, amino, halogen, and nonsubstituted or substituted straight or branched $C_{1-5}$ alkyl, wherein the substituted alkyl is substituted with halogen;

$R^2$ is hydroxy, amino, cyano, halogen, $C_{1-3}$ straight or branched alkyl, or $C_{1-3}$ straight or branched alkoxy;

n is an integer of 0~8;

X and Y are independently CH or N; and

Z is sulfinyl or sulfonyl).

In a preferred embodiment of the present invention, $R^1$ can be phenyl substituted with one or more substituents selected from the group consisting of F, Cl, Br, I, and $CF_3$.

In another embodiment of the present invention, $R^1$ is substituted phenyl, the substituted phenyl is substituted with one or more substituents selected from the group consisting of halogen and $CF_3$;

any one of X and Y is CH and the other is N; and

Z is S(O).

In another embodiment of the present invention, if any one of X and Y is CH, the other can be N.

In another embodiment of the present invention, if X is CH, Y is N.

In another embodiment of the present invention, the compound represented by formula 1 can be any one compound selected from the following compound group, or a pharmaceutically acceptable salt thereof:

(1) 1-((4-fluorophenyl)sulfinyl)isoquinoline;

(2) 4-((4-fluorophenyl)sulfinyl)quinoline;

(3) 1-((2,4-difluorophenyl)sulfinyl)isoquinoline;

(4) 1-((4-chlorophenyl)sulfinyl)isoquinoline; and (5) 1-((4-(trifluoromethyl)phenyl)sulfinyl)isoquinoline.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

In addition, the present invention includes not only the compound represented by formula 1 but also a pharmaceutically acceptable salt thereof, and a solvate, an optical isomer, or a hydrate possibly produced from the same.

In another aspect of the present invention, the present invention provides a preparation method of a compound represented by formula 1 comprising a step of preparing a compound represented by formula 1 from a compound represented by formula 4; as shown in reaction formula 1 below.

[Reaction Formula 1]

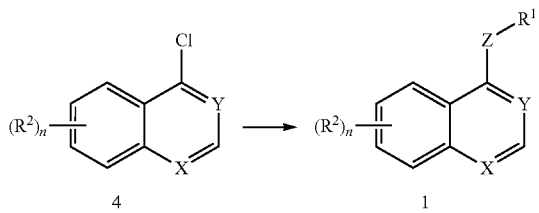

(In reaction formula 1, $R^1$, $R^2$, n, X, Y and Z are as defined in formula 1 above).

In another embodiment of the present invention, when Z is sulfinyl or sulfonyl, the compound represented by formula 1 can be understood to be a compound represented by Formula 1″.

The preparation method can comprises the following steps, as shown in reaction formula 3 below:

preparing a compound represented by formula 1′ by reacting a compound represented by formula 4 with a compound represented by formula 3; and preparing a compound represented by formula 1″ from the compound represented by formula 1′ prepared in the above step.

[Reaction Formula 3]

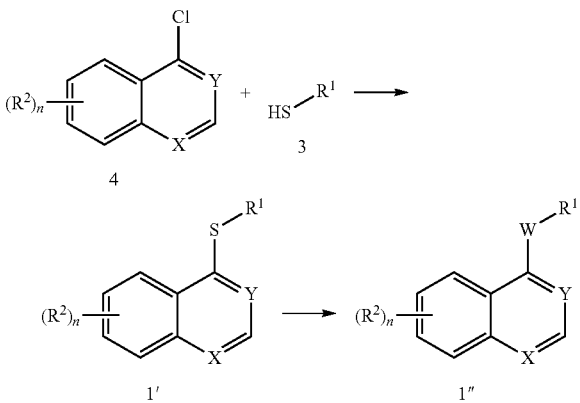

(In reaction formula 3, $R^1$, $R^2$, n, X and Y are as defined in formula 1 above; and W is sulfinyl or sulfonyl).

In the step of preparing a compound represented by formula 1' by reacting a compound represented by formula 4 with a compound represented by formula 3, the usable solvent is exemplified by $H_2O$, ethanol, tetrahydrofuran (THF), dichloromethane, toluene, acetonitrile and dimethylformamide, and ethanol is more preferred herein. In addition, the reaction time is not particularly limited, but it is preferable to react for 5 to 30 hours, 10 to 20 hours, or about 12 hours. Further, the reaction temperature is not particularly limited, but it is preferable to perform at room temperature or 20 to 30° C.

In the most preferred embodiment of the present invention, the methods that can be carried out as in the following examples of the present invention, and can be changed such as the aspects and conditions of the experiments are also included in the scope of the present invention.

In addition, in the step of preparing a compound represented by formula 1" from the compound represented by formula 1' prepared in the above step, the above step can be considered a reaction of introducing a sulfinyl group or a sulfonyl group, but not always limited thereto. For example, the reaction can be carried out using m-chloroperoxybenzoic acid or the like. As a solvent, $C_1$-$C_4$ alcohol, acetone, acetonitrile, benzene, 2-butanone, chlorobenzene, chloroform, cyclohexane, toluene, 1,2-dichloromethane (DCM), heptane, hexane, etc. can be used, and chloroform can be preferably used. The reaction time is not particularly limited, but it is preferable to react for 5 to 30 hours, 10 to 20 hours, or about 12 hours. Further, the reaction temperature is not particularly limited, but it is preferable to perform at room temperature or 20 to 30° C.

In the most preferred embodiment of the present invention, the methods that can be carried out as in the following examples of the present invention, and can be changed such as the aspects and conditions of the experiments are also included in the scope of the present invention.

In another aspect of the present invention, the present invention provides a pharmaceutical composition for preventing or treating autophagy related diseases containing a compound represented by formula 1 or a pharmaceutically acceptable salt thereof as an active ingredient.

Herein, the compound represented by formula 1 or the pharmaceutically acceptable salt thereof can be understood as an active ingredient for regulating autophagy activity.

In a preferred embodiment of the present invention, the autophagy activity was regulated by the compound represented by formula 1 of the present invention as shown in Experimental Example 1.

Particularly, autophagy may be a process mediated by the exposure of cells to stress, such as nutrient supply blockage, bacterial invasion, and the like. The compound represented by formula 1 of the present invention can be understood as an active ingredient that regulates the autophagy activity, exhibits an anti-inflammatory effect capable of suppressing an inflammatory response through inhibition of NO production and inflammation-related factors such as IL-6 and IL-β, has an effect of inhibiting melanogenesis, has an inhibitory effect on metabolic syndrome such as fatty liver suppression and obesity suppression, and exhibits a significant effect on other autophagy related diseases.

In addition, the compound represented by formula 1 of the present invention has been found to be a safe compound in general cytotoxicity test, cardiotoxicity evaluation, skin toxicity evaluation, ocular toxicity evaluation, and liver damage evaluation, suggesting that it can be provided as an active ingredient of a safer therapeutic agent in the living body.

In another embodiment of the present invention, the autophagy related disease includes all the diseases that have been identified, studied, or reported to be related to autophagy activity, and includes, for example, cancer, atherosclerosis, neurodegenerative diseases, Alzheimer's disease, Parkinson's disease, amyotrophic lateral sclerosis, Huntington's disease, spinocerebellar ataxia, oculopharyngeal muscular dystrophy, prion disease, fatal familial insomnia, alpha-1 antitrypsin deficiency, dentatorubral pallidoluysian atrophy, frontotemporal dementia, progressive supranuclear palsy, x-linked spinobulbar muscular atrophy and neuronal intranuclear hyaline inclusion disease.

In another embodiment of the present invention, the autophagy related disease can be a metabolic syndrome-related disease (otherwise a metabolic disease), and includes, for example, obesity, diabetes, dyslipidemia, alcoholic fatty liver, non-alcoholic fatty liver, hypertension, arteriosclerosis, hyperlipidemia and hyperinsulinemia, etc.

In another embodiment of the present invention, the autophagy related disease can be an inflammatory disease, and for example, can be a disease that can be improved, prevented, or treated by inhibiting NO production, IL-6 or IL-1β expression, and the like. The inflammatory disease can be, for example, an intestinal disease, ulcerative colitis, Crohn's disease, arthritis, dermatitis, atopic dermatitis, ophthalmitis, keratitis, hepatitis, non-alcoholic hepatitis, and the like.

In another embodiment of the present invention, the autophagy related disease can be a disease related to melanogenesis, and can be a skin disease caused by melanin overproduction, for example, skin hyperpigmentation.

Herein, the skin disease caused by melanin overproduction can be understood as a disease including the lesions caused by pigmentation such as melasma, freckles, lentigo and age spots.

In the above-mentioned autophagy diseases, the compound represented by formula 1 of the present invention or a pharmaceutically acceptable salt thereof can exhibit medically useful effects such as prevention, amelioration, and treatment of the diseases. This is supported by the Examples and Experimental Examples of the present specification, and thus, a pharmaceutical composition containing the same as an active ingredient can be provided.

On the other hand, a pharmaceutical composition for preventing or treating the following diseases can be provided purely based on those shown in Experimental Examples of the present invention not limited to the autophagy related diseases, that is regardless of the above-described autophagy-related theories or mechanisms deviating from the effects and explanations related to autophagy described herein.

In another aspect of the present invention, the present invention provides a pharmaceutical composition for preventing or treating inflammatory or metabolic diseases containing a compound represented by formula 1 or a pharmaceutically acceptable salt thereof as an active ingredient.

Herein, the inflammatory disease can be a disease that can be improved, prevented, or treated from inhibiting NO production, IL-6 or IL-1β expression, and the like. The inflammatory disease can be, for example, an intestinal disease, ulcerative colitis, Crohn's disease, arthritis, dermatitis, atopic dermatitis, ophthalmitis, keratitis, hepatitis, non-alcoholic hepatitis, and the like.

As shown in the following Experimental Examples and FIGS. 3, 4 and 5 of the present invention, the compound represented by formula 1 was confirmed to have the effect of inhibiting NO production and IL-6 or IL-1β expression. This effect can be explained as being related to the autophagy regulation effect or it can be explained as an independent effect, but not always limited thereto. Rather, regardless of this, a pharmaceutical composition for preventing or treating inflammatory diseases can be provided from the inflammatory response inhibitory effect demonstrated herein.

In addition, the metabolic disease can be understood as metabolic syndrome, for example, obesity, diabetes, dyslipidemia, alcoholic fatty liver, non-alcoholic fatty liver, hypertension, arteriosclerosis, hyperlipidemia, hyperinsulinemia, etc.

As shown in the following Experimental Examples and FIGS. 7 and 8 of the present invention, the compound represented by formula 1 was confirmed to have the effect of inhibiting fatty liver. This effect can be explained as being related to the autophagy regulation effect or it can be explained as an independent effect, but not always limited thereto. Rather, regardless of this, a pharmaceutical composition for preventing or treating metabolic diseases can be provided from the fatty liver and liver damage inhibitory effect demonstrated herein.

In addition, in another aspect of the present invention, the present invention provides a pharmaceutical composition for preventing or treating skin hyperpigmentation containing a compound represented by formula 1 or a pharmaceutically acceptable salt thereof as an active ingredient.

Herein, the skin hyperpigmentation can be, for example, a skin disease caused by melanin overproduction, and can be a disease including the lesions caused by pigmentation such as melasma, freckles, lentigo, and senile pigmentation spots.

Figure 6A:
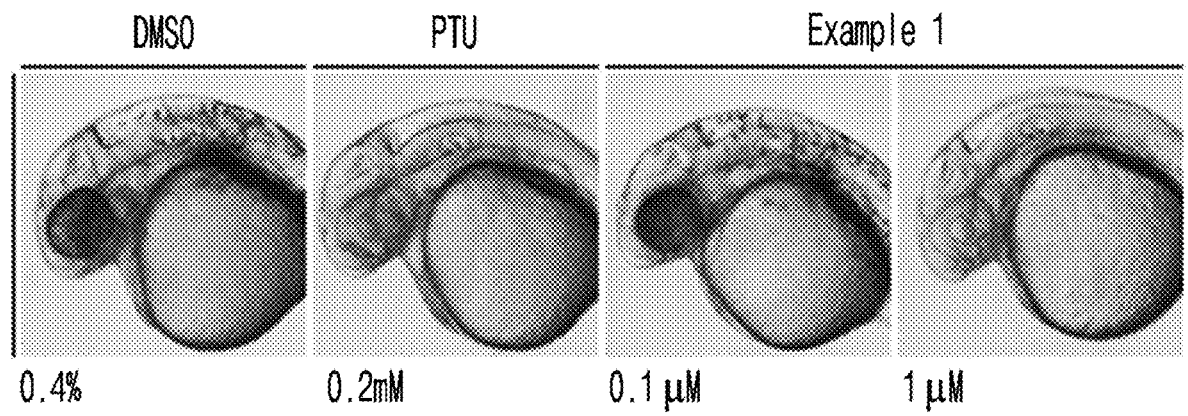
FIG. 6A is a set of zebrafish juvenile fish photographs confirming the effect of inhibiting melanocyte formation at 22 hours after the treatment of the compound of Example 1 of the present invention in fertilized zebrafish eggs 10 hours after fertilization (32 hours after fertilization).

As shown in the following Experimental Examples and FIGS. 6A to 6C of the present invention, the compound represented by formula 1 of the present invention was confirmed to excellently inhibit melanogenesis at all time points before and after the formation of melanocytes. Therefore, a pharmaceutical composition for preventing or treating skin hyperpigmentation containing the same as an active ingredient can be provided.

The compound represented by formula 1 can be administered in various oral and parenteral formulations during clinical administration. In the case of formulation, it can be prepared using generally used diluents or excipients such as fillers, extenders, binders, wetting agents, disintegrating agents and surfactants.

Solid formulations for oral administration are exemplified by tablets, pills, granules, capsules, and troches, etc. These solid formulations are prepared by mixing one or more compounds of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, flavoring agents and preservatives in addition to generally used simple diluents such as water and liquid paraffin.

Formulations for parenteral administration are sterilized aqueous solutions, water-insoluble excipients, suspensions, emulsions, lyophilized preparations and suppositories.

Water insoluble excipients and suspensions can contain propylene glycol, polyethylene glycol, vegetable oil like olive oil, injectable ester like ethylolate, etc. Suppositories can contain witepsol, macrogol, tween 61, cacao butter, laurin butter, glycerol, gelatin, etc.

In addition, the compound of the present invention can be formulated as creams, ointments, gels, lotions, solutions, or transdermal preparations such as patches.

The effective dosage of the compound of the present invention to the human body can be determined according to age, may vary depending on the patient's age, weight, gender, administration method, health condition, and severity of disease, and is generally about 0.001~100 mg/kg/day, and preferably 0.01~35 mg/kg/day. The dosage is generally 0.07~7000 mg/day, and preferably 0.7~2500 mg/day based on an adult patient weighing 70 kg, which can be administered once or several times a day at intervals of a certain time depending on the judgment of a doctor or a pharmacist.

In another aspect of the present invention, the present invention provides a method for treating autophagy related diseases comprising a step of administering a compound represented by formula 1 or a pharmaceutically acceptable salt thereof to a subject in a therapeutically effective amount.

At this time, the autophagy related disease is as described herein.

The therapeutically effective amount refers to an amount capable of treating, preventing, or ameliorating the symptoms or conditions of a subject when administered into the body, depending on the administration method. In addition, the amount may vary depending on the weight, age, gender, condition, and family history of the subject to be administered. In the treatment method of the present invention, different dosages may be determined according to the different conditions for each subject.

The "effective amount" is an amount effective to treat autophagy related diseases, such as cancer, atherosclerosis, neurodegenerative disease, Alzheimer's disease, Parkinson's disease, amyotrophic lateral sclerosis, Huntington's disease, spinocerebellar ataxia, oculopharyngeal muscular dystrophy, prion disease, fatal familial insomnia, alpha-1 antitrypsin deficiency, dentatorubral pallidoluysian atrophy, frontotemporal dementia, progressive supranuclear palsy, x-linked spinobulbar muscular atrophy or neuronal intranuclear hyaline inclusion disease. In another embodiment of the present invention, the "effective amount" of a compound means more than the minimum amount capable of regulating autophagy activity.

The compound and composition according to the present invention can be administered using any route of administration in any amount effective to treat a disease. The exact amount required may vary from subject to subject, depending on the subject's species, age, and general condition, the severity of the infection, the particular agent, its mode of administration, and the like. The compound of the present invention is frequently formulated in a dosage unit form for ease of administration and uniformity of dosage. The "dosage unit form" as used herein refers to a physically discrete unit of an agent suitable for the subject to be treated. It will also be understood that the total daily dosage of the compound and composition of the present invention can be determined by an attending physician within the scope of a sound medical judgment. The particular effective dosage level for any particular subject or organism depends on the following a variety of factors: the disease to be treated and the severity of the disease; activity of the particular compound used; the particular composition used; age, weight, general health, gender and diet of the subject; administration time, administration route, and excretion rate of the particular compound used; duration of treatment; the particular compound used alone or co-administered drugs, and other factors than those well known in the medical art.

The term "subject" refers to a subject for whom the compound, the pharmaceutically acceptable salt thereof, or the pharmaceutical composition provided in the present invention is desired. Alternatively, the subject means a subject in need of the effect of prevention, amelioration, or treatment of autophagy related diseases. For example, the subject can be an animal, preferably a non-mammal or a mammal, more preferably a livestock or a human, and most preferably a human.

In another aspect, the present invention provides a health functional food composition or a cosmetic composition as follows.

In an aspect of the present invention, the present invention provides a health functional food composition for preventing or ameliorating autophagy related diseases containing a compound represented by formula 1 or a pharmaceutically acceptable salt thereof as an active ingredient.

Herein, the autophagy related disease includes all the diseases that have been identified, studied, or reported to be related to autophagy activity, and includes, for example, cancer, atherosclerosis, neurodegenerative diseases, Alzheimer's disease, Parkinson's disease, amyotrophic lateral sclerosis, Huntington's disease, spinocerebellar ataxia, oculopharyngeal muscular dystrophy, prion disease, fatal familial insomnia, alpha-1 antitrypsin deficiency, dentatorubral pallidoluysian atrophy, frontotemporal dementia, progressive supranuclear palsy, x-linked spinobulbar muscular atrophy and neuronal intranuclear hyaline inclusion disease.

In another aspect of the present invention, the present invention provides a health functional food composition for preventing or ameliorating inflammatory or metabolic diseases containing a compound represented by formula 1 or a pharmaceutically acceptable salt thereof as an active ingredient.

Herein, the inflammatory disease can be a disease that can be improved, prevented, or treated from inhibiting NO production, IL-6 or IL-1β expression, and the like. For example, the inflammatory disease can be an intestinal disease, ulcerative colitis, Crohn's disease, arthritis, dermatitis, atopic dermatitis, ophthalmitis, keratitis, hepatitis, non-alcoholic hepatitis, and the like.

In addition, the metabolic disease can be understood as metabolic syndrome, for example, obesity, diabetes, dyslipidemia, alcoholic fatty liver, non-alcoholic fatty liver, hypertension, arteriosclerosis, hyperlipidemia, hyperinsulinemia, etc.

Further, in another aspect of the present invention, the present invention provides a cosmetic composition for whitening containing a compound represented by formula 1 or a pharmaceutically acceptable salt thereof as an active ingredient.

Herein, the cosmetic composition can inhibit melanogenesis by containing the compound represented by formula 1 as an active ingredient. Therefore, the cosmetic composition can be effectively used as a cosmetic composition for whitening, when used for the purpose of inhibiting melanin formation in the skin, hair, and particularly in the eye.

The compound represented by formula 1, a component of the cosmetic composition for whitening, was confirmed to be a toxicologically safe component to the living body such as cells, skin, and eyes, as shown in Experimental Examples of the present invention. Therefore, the compound of the present invention can be applied without any special restrictions on the site to be applied in order to inhibit the formation of melanocytes and the melanin synthesis.

In a preferred embodiment of the present invention, as shown in the following Experimental Examples and FIG. 6, the compound represented by formula 1 of the present invention significantly inhibited the formation of melanocytes, and inhibited the melanin synthesis of the already generated melanocytes. Therefore, the cosmetic composition can be provided as a cosmetic composition for whitening.

In particularly, the composition can be effectively used for a subject suffering from skin hyperpigmentation, for example, can be usefully used for the lesions caused by pigmentation such as melasma, freckles, lentigo, and senile pigmentation spots.

Alternatively, the composition can be effectively used for the purpose of skin whitening, even if the subject is not suffering from the disease.

On the other hand, the formulation of the cosmetic composition of the present invention is not particularly limited and can be arbitrarily selected and applied. The composition can be prepared and used in various formulations like the conventional cosmetic formulations such as external skin ointment, essence, whitening cream, lotion, emulsion, pack, general lotion, skin milk, cream, serum, beauty soap, softening lotion, medicinal lotion, hair tonic, body cleanser, and oil gel, etc.

Hereinafter, the present invention will be described in detail by the following examples and experimental examples.

However, the following examples and experimental examples are only for illustrating the present invention, and the contents of the present invention are not limited thereto.

<Example 1> Preparation of 1-((4-Fluorophenyl)Sulfinyl)Isoquinoline

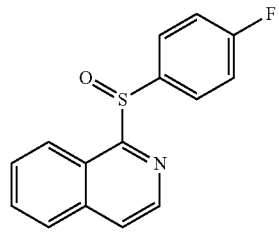 [SMILES: O=S(c1ccc(F)cc1)c1nccc2ccccc12]

Step 1: Preparation of 1-((4-Fluorophenyl)Thio)Isoquinoline

4-Fluorobenzenethiol (1.436 mL, 13.447 mmol) was added to ethanol containing 1-chloroisoquinoline (2 g, 12.225 mmol). The reactant was stirred at room temperature for 12 hours. The mixture was concentrated in vacuo. The crude product was purified by silica gel column chromatography using ethyl acetate/hexane to give a target compound (686 mg, 22%).

$^1$H NMR (400 MHz, DMSO-d6) δ 8.28 (d, J=8.24 Hz, 1H), 8.18 (d, J=5.49 Hz, 1H), 7.99 (d, J=8.24 Hz, 1H), 7.81-7.85 (m, 1H), 7.72-7.77 (m, 1H), 7.61-7.66 (m, 3H), 7.29-7.35 (m, 2H).

Step 2: Preparation of 1-((4-Fluorophenyl)Sulfinyl)Isoquinoline

The 1-((4-fluorophenyl)thio)isoquinoline (850 mg, 3.329 mmol) prepared in step 1 was dissolved in THF/water. Oxone (574.53 mg, 3.329 mmol) was added to the mixture, followed by stirring at room temperature for 12 hours. The mixture was diluted with water, extracted with ethyl acetate, washed with brine, dried over anhydrous sodium sulfate and concentrated in vacuo. The crude product was purified by silica gel column chromatography using ethyl acetate/hexane to give a target pure compound (218 mg. 24%).

¹H NMR (400 MHz, CDCl₃) δ 8.79 (d, J=8.54 Hz, 1H), 8.47 (d, J=5.49 Hz, 1H), 7.52-7.76 (m, 6H), 6.99 (t, J=8.54 Hz, 2H).

<Example 2> Preparation of 4-((4-Fluorophenyl)Sulfinyl)Quinoline

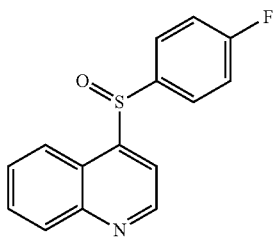 [SMILES: O=S(c1ccc(F)cc1)c1ccnc2ccccc12]

Step 1: Preparation of 4-((4-Fluorophenyl)Thio)Quinolone
The experiment was performed as described in step 1 of Example 1, except that 4-chloroquinoline (250 mg, 1.528 mmol) was used instead of 1-chloroisoquinoline.

4-Fluorobenzenethiol (250 mg, 1.528 mmol) was added to ethanol containing 4-chloroquinoline (250 mg, 1.528 mmol). The reactant was stirred at room temperature for 12 hours. The mixture was concentrated in vacuo. The crude product was purified by silica gel column chromatography using ethyl acetate/hexane to give a target compound (185.0 mg, 47.4%).

¹HNMR (400 MHz, CDCl₃) δ 8.565 (d, J=4.88 Hz, 1H), 8.178 (d, J=9.16 Hz, 1H), 8.069 (d, J=8.24 Hz, 1H), 7.730 (m, 1H), 7.583 (m, 3H), 7.181 (t, J=17.40, 2H), 6.673 (d, J=4.58, 1H).

Step 2: Preparation of 4-((4-Fluorophenyl)Sulfinyl)Quinolone
A target compound was prepared by the similar manner to the method described in step 2 of Example 1, except that the 4-((4-fluorophenyl)thio)quinolone (280 mg, 1.097 mmol) prepared in step 1 was used instead of 1-((4-fluorophenyl)thio)isoquinoline.

¹HNMR (400 MHz, CDCl₃) δ 9.124 (d, J=4.58 Hz, 1H), 8.156 (m, 2H), 7.974 (d, J=8.85 Hz, 1H), 7.711 (m, 3H), 7.572 (m, 1H), 7.096 (t, J=17.09 Hz, 2H).

<Example 3> Preparation of 1-((2,4-Difluorophenyl)Sulfinyl)Isoquinoline

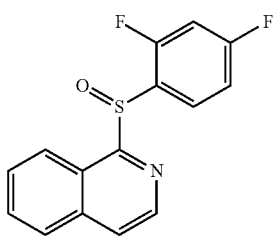 [SMILES: O=S(c1ccc(F)cc1F)c1nccc2ccccc12]

Step 1: Preparation of 1-((2,4-Difluorophenyl)Thio)Isoquinoline
The experiment was performed as described in step 1 of Example 1, except that 2,4-difluorobenzenethiol (1.527 mmol) was used instead of 4-fluorobenzenethiol.

2,4-Difluorobenzenethiol (1.527 mmol) was added to ethanol containing 1-chloroquinoline (0.25 g, 1.527 mmol). The reactant was stirred at room temperature for 12 hours. The mixture was concentrated in vacuo. The crude product was purified by silica gel column chromatography using ethyl acetate/hexane to give a target compound (42%).

¹HNMR (400 MHz, CDCl₃) δ 8.308 (d, J=8.24 Hz, 1H), 8.159 (d, J=5.95 Hz, 1H), 7.778 (d, J=8.24 Hz, 1H), 7.690 (t, J=14.95 Hz, 1H), 7.602 (m, 2H), 7.367 (d, J=5.49 Hz, 1H), 6.961 (m, 2H).

Step 2: Preparation of 1-((2,4-Difluorophenyl)Sulfinyl)Isoquinoline
A target compound was prepared by the similar manner to the method described in step 2 of Example 1, except that the 1-((2,4-difluorophenyl)thio)isoquinoline (200 mg) prepared in step 1 was used (57%).

¹HNMR (400 MHz, CDCl₃) δ 8.685 (d, J=8.24 Hz, 1H), 8.579 (d, J=5.49 Hz, 1H), 8.085 (m, 1H), 7.898 (d, J=8.24 Hz, 1H), 7.742 (m, 3H), 7.074 (m, 1H), 6.747 (m, 1H).

<Example 4> Preparation of 1-((4-Chlorophenyl)Sulfinyl)Isoquinoline

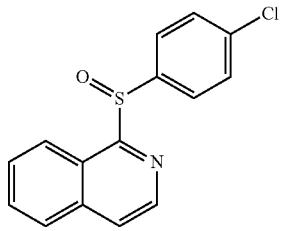 [SMILES: O=S(c1ccc(Cl)cc1)c1nccc2ccccc12]

Step 1: Preparation of 1-((4-Chlorophenyl)Thio)Isoquinoline
A target compound was prepared by the similar manner to the method described in step 1 of Example 1, except that 4-chlorobenzenethiol (1.527 mmol) was used instead of 4-fluorobenzenethiol (48%).

¹HNMR (400 MHz, CDCl₃) δ 8.313 (d, J=8.24, 1H), 8.220 (d, J=5.80 Hz, 1H), 7.782 (d, J=8.24 Hz, 1H), 7.690 (m, 1H), 7.607 (m, 1H), 7.510 (m, 2H), 7.379 (m, 3H).

Step 2: Preparation of 1-((4-Chlorophenyl)Sulfinyl)Isoquinoline
A target compound was prepared by the similar manner to the method described in step 2 of Example 1, except that the 1-((4-chlorophenyl)thio)isoquinoline (200 mg) prepared in step 1 was used (25%).

¹HNMR (400 MHz, CDCl₃) δ 8.903 (d, J=8.54 Hz, 1H), 8.558 (d, J=5.49 Hz, 1H), 7.871 (d, J=8.24 Hz, 1H), 7.750 (m, 3H), 7.706 (d, J=5.49 Hz, 1H), 7.648 (m, 1H), 7.374 (d, J=8.54 Hz, 2H).

<Example 5> Preparation of 1-((4-(Trifluoromethyl)Phenyl)Sulfinyl) Isoquinoline

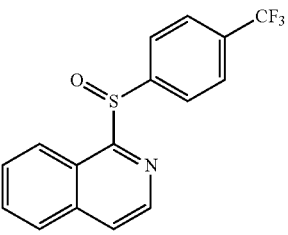 [SMILES: O=S(c1ccc(C(F)(F)F)cc1)c1nccc2ccccc12]

Step 1: Preparation of 1-((4-(Trifluoromethyl)Phenyl)Thio)Isoquinoline

A target compound was prepared by the similar manner to the method described in step 1 of Example 1, except that 4-(trifluoromethyl)benzenethiol (1.527 mmol) was used instead of 4-fluorobenzenethiol (59%).

¹HNMR (400 MHz, CDCl₃) δ 8.335 (d, J=8.24 Hz, 1H), 8.269 (d, J=5.49 Hz, 1H), 7.811 (d, J=7.93 Hz, 1H), 7.710 (m, 1H), 7.630 (m, 5H), 7.465 (d, J=5.49 Hz, 1H).

Step 2: Preparation of 1-((4-(Trifluoromethyl)Phenyl)Sulfinyl)Isoquinoline

A target compound was prepared by the similar manner to the method described in step 2 of Example 1, except that the 1-((4-(trifluoromethyl)phenyl)thio)isoquinoline (250 mg) was used prepared in step 1 (62%).

¹HNMR (400 MHz, CDCl₃) δ 8.972 (d, J=8.54 Hz, 1H), 8.558 (d, J=5.49 Hz, 1H), 7.946 (d, J=8.24 Hz, 2H), 7.880 (d, J=8.24 Hz, 1H), 7.714 (m, 5H).

Structural formulas of the compounds prepared in Examples 1~7 are shown in Table 1 below.

<Comparative Example 1> Preparation of 1-((4-Fluorophenyl)Thio) Isoquinoline

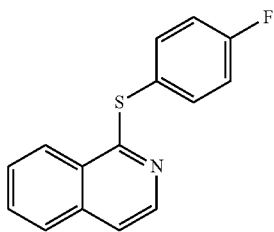 [SMILES: Fc1ccc(Sc2nccc3ccccc23)cc1]

Step 1: Preparation of 1-((4-Fluorophenyl)Thio)Isoquinoline

4-Fluorobenzenethiol (1.436 mL, 13.447 mmol) was added to ethanol containing 1-chloroisoquinoline (2 g, 12.225 mmol). The reactant was stirred at room temperature for 12 hours. The mixture was concentrated in vacuo. The crude product was purified by silica gel column chromatography using ethyl acetate/hexane to give a target compound (686 mg, 22%).

¹H NMR (400 MHz, DMSO-d6) δ 8.28 (d, J=8.24 Hz, 1H), 8.18 (d, J=5.49 Hz, 1H), 7.99 (d, J=8.24 Hz, 1H), 7.81-7.85 (m, 1H), 7.72-7.77 (m, 1H), 7.61-7.66 (m, 3H), 7.29-7.35 (m, 2H).

<Comparative Example 2> Preparation of 1-((4-Fluorophenyl) Sulfonyl)Isoquinoline

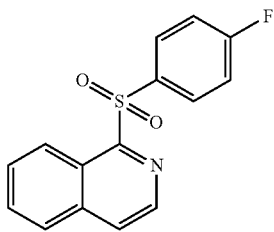 [SMILES: O=S(=O)(c1ccc(F)cc1)c1nccc2ccccc12]

Step 1: Preparation of 1-((4-Fluorophenyl)Thio)Isoquinoline

4-Fluorobenzenethiol (1.436 mL, 13.447 mmol) was added to ethanol containing 1-chloroisoquinoline (2 g, 12.225 mmol). The reactant was stirred at room temperature for 12 hours. The mixture was concentrated in vacuo. The crude product was purified by silica gel column chromatography using ethyl acetate/hexane to give a target compound (686 mg, 22%).

¹H NMR (400 MHz, DMSO-d6) δ 8.28 (d, J=8.24 Hz, 1H), 8.18 (d, J=5.49 Hz, 1H), 7.99 (d, J=8.24 Hz, 1H), 7.81-7.85 (m, 1H), 7.72-7.77 (m, 1H), 7.61-7.66 (m, 3H), 7.29-7.35 (m, 2H).

Step 2: Preparation of 1-((4-Fluorophenyl)Sulfonyl)Isoquinoline 1-((4-Fluorophenyl)thio)isoquinoline (850 mg, 3.329 mmol) was dissolved in THF/water. Oxone (2.2 eq, 7.3238 mmol) was added to the mixture, followed by stirring at room temperature for 12 hours. The mixture was diluted with water, extracted with ethyl acetate, washed with brine, dried over anhydrous sodium sulfate and concentrated in vacuo. The crude product was purified by silica gel column chromatography using ethyl acetate/hexane to give a target pure compound (4 c, 66%).

¹HNMR (400 MHz, CDCl₃) δ 8.79 (d, J=8.54 Hz, 1H), 8.47 (d, J=5.49 Hz, 1H), 7.52-7.76 (m, 6H), 6.99 (t, J=8.54 Hz, 2H).

<Experimental Example 1> Evaluation of Autophagy Regulatory Activity

In order to evaluate the autophagy regulating activity of the novel isoquinoline derivative according to the present invention, the following experiment was performed.

<1-1> Analysis of Autophagy Indices

The conversion from LC3-I to LC3-II, which is an autophagy index, was analyzed by Western blotting.

Particularly, for Western blotting, RAW264.7 cells, which are mouse macrophages, were aliquoted into 60 mm cell culture dishes at the density of 20×10⁵ cells/dish and cultured for one day. The cells were treated with the compound of Example 1 of the present invention using DMSO at the concentrations of 1, 5, 10 and 20 μM, followed by culture in a 37° C., CO₂ incubator for one day. After detaching the cells using 0.1% trypsin-EDTA, the cells were collected by centrifugation. The cells were lysed using a lysis buffer (RIPA lysis buffer) (50 mM Tris, pH 7.4, 0.1% SDS, 1% NP-40, 150 mM NaCl, 1 mM PMSF, 10 mM NaF, 10 ug/ml aprotinin, 10 ug/ml leupeptin, 10 mM Na₃VO₄) and then centrifuged to obtain a cell lysate. The obtained cell lysate was quantified for protein, and a cell lysate containing the same amount (50 ug) of protein was separated by electrophoresis on a 4-12% Bis-Tris acrylamide gel. Proteins in the obtained cell lysate were quantified, and the cell lysate containing the same amount (50 ug) of protein was separated by electrophoresis on a 4-12% Bis-Tris acrylamide gel. After the isolated proteins were transferred to a PVDF membrane, Western blotting was performed. Blocking of the PVDF membrane was performed in TBST (25 mM Tris, pH 7.5, 150 mM NaCl, 0.1% Tween-200) containing 5% skim milk for 1 hour. An anti-LC3 antibody was used as the primary antibody. As an internal standard protein, anti-GAPDH purchased from Santacruz was used. The primary antibody was reacted at room temperature for 3 hours. The membrane was washed three times with TBST buffer, and reacted with a secondary antibody (horseradish peroxidase-conjugated anti-goat IgG) at room temperature for 2 hours. Upon completion of the reaction, the PVDF membrane was washed three times with TBST buffer, reacted with ECL solution, and chemiluminescence was obtained using an imaging device. The results confirmed by Western blotting are shown in FIG. 1.

FIG. 1 is a set of Western blot diagrams confirming the conversions of LC3-I and LC3-II according to the treatment of the compound of Example 1 of the present invention at the concentrations of 1, 5, 10, and 20 μM in Raw 264.7 mouse macrophages.

<1-2> Intracellular Autophagosome Visualization Analysis

In order to detect autophagosomes formed by regulation of autophagy, analysis of observation was performed using acridine orange, which selectively stains acidic vesicles in the cytoplasm.

Particularly, the fluorescence characteristics of autophagosomes are changed by protonation of acridine orange accumulated due to acidification in the cytoplasm. An experiment was performed as follows using these fluorescence characteristics.

Raw 264.7 mouse macrophages were aliquoted in a 96-well plate at the density of $5\times10^4$ cells/well and stabilized in a 37° C., 5% $CO_2$ incubator for 24 hours. The Raw 264.7 cells were treated with the compound of Example 1 at the concentrations of 5, 10, 20 and 50 μM. After 1 hour, the cells were treated with 1 ug/ml of LPS and cultured for 24 hours. After removing the medium and replacing it with a medium containing 5 μM acridine orange, the cells were stained in a 37° C., 5% $CO_2$ incubator for 15 minutes. After staining was completed, the cells were washed with PBS, and the formation of intracellular autophagosomes was observed under a fluorescence microscope. The results visualized by acridine orange fluorescence are shown in FIG. 2.

Figure 2:
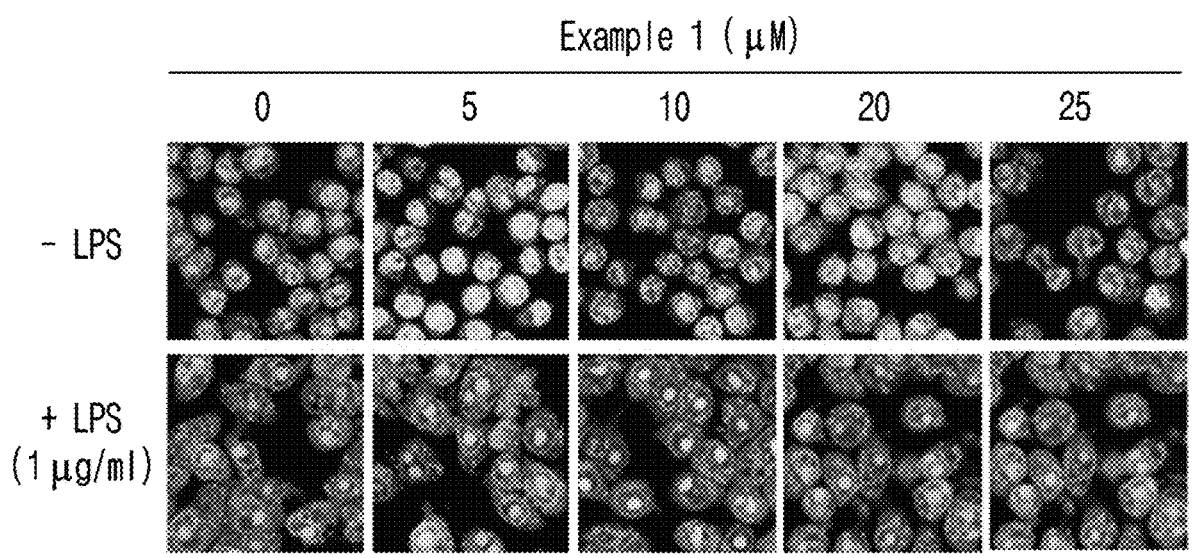
FIG. 2 is a set of fluorescence micrographs confirming the changes in autophagosomes observed after the treatment of the compound of Example 1 of the present invention at the concentrations of 5, 10, 20, and 50 μM in Raw 264.7 mouse macrophages under the conditions for inducing inflammatory responses by lipopolysaccharide (LPS) treatment.

FIG. 2 is a set of fluorescence micrographs confirming the changes in autophagosomes observed after the treatment of the compound of Example 1 of the present invention at the concentrations of 5, 10, 20, and 50 μM in Raw 264.7 mouse macrophages in which inflammatory response was induced by treatment of LPS.

<Experimental Example 2> Evaluation of Disease-Related Drug Efficacy

<2-1> Measurement of Anti-Inflammatory (NO) Activity

Macrophages are cells that cause inflammatory responses. These cells play a biodefense role by producing NO and cytokines when stress or stimulation occurs. NO plays an essential role in the innate immune response in response to pathogens such as viruses and bacteria, and L-arginine is produced by NO synthase (NOS). NOS is divided into cNOS (constitutive NOS) and iNOS (inducible NOS). Among them, iNOS induces inflammatory responses by generating a large amount of NO by stimulation such as stress or cytokines.

In order to confirm the effect of the compound of Example 1 of the present invention on NO production in Raw 264.7 mouse macrophages in which inflammatory response was induced by LPS, an experiment was performed as follows.

Raw 264.7 mouse macrophages were aliquoted in a 96-well plate at the density of $1\times10^5$ cells/well and stabilized in a 37° C., 5% $CO_2$ incubator for 24 hours. The Raw 264.7 cells were treated with the compound of Example 1 by concentration. After 1 hour, the cells were treated with 1 ug/ml of LPS and cultured for 24 hours. For the measurement of NO production, 40 mg/ml of Griess reagent was prepared and it was mixed with the culture supernatant at the same ratio. The mixture was reacted at room temperature for 15 minutes, and absorbance was measured at 540 nm. Based on the results obtained therefrom, the cell viability and NO production rate were expressed as percentages in terms of LPS. The results are shown in Table 2 below. Meanwhile, the results for the compound of Example 1 are presented in FIG. 3.

TABLE 1

|  | Cell viability (% of control) | NO production (% of control) |
|---|---|---|
| Example 1 | 90 | 40 |
| Example 2 | 100 | 26 |
| Example 3 | 103 | 30 |
| Example 4 | 96 | 40 |
| Example 5 | 101 | 25 |
| Comparative Example 1 | 95 | 70 |
| Comparative Example 2 | 73 | 65 |

Figure 3:
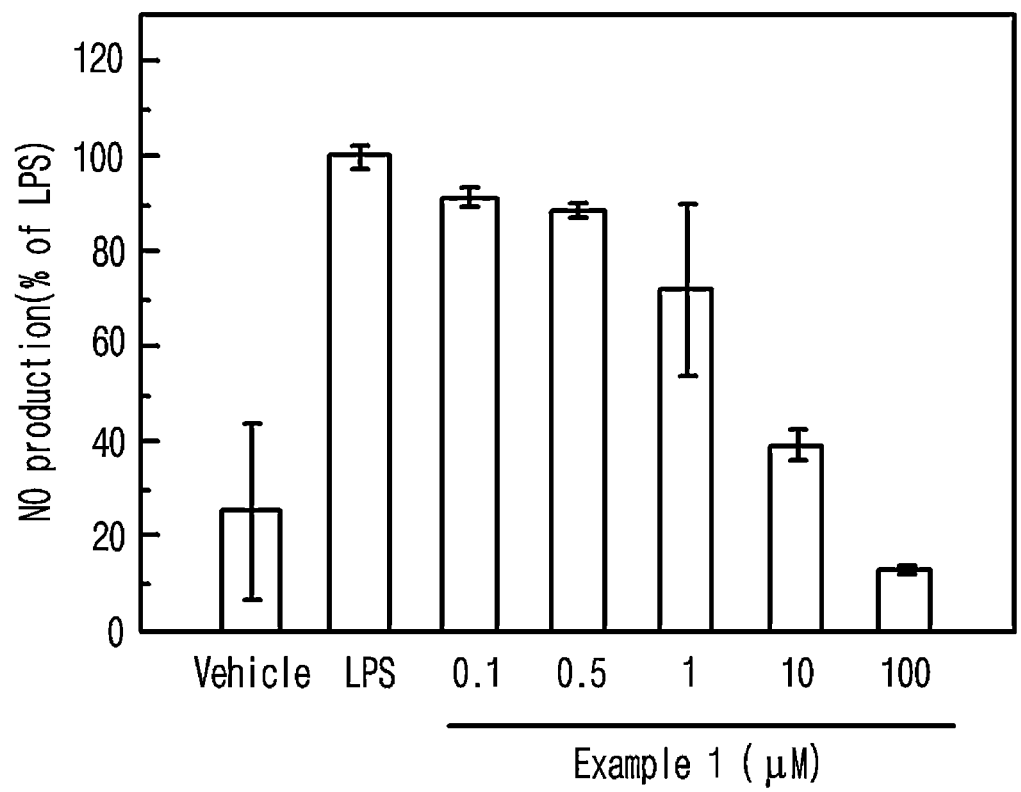
FIG. 3 is a set of graphs illustrating the effect of the compound of Example 1 on the NO production and cell viability in LPS-treated Raw 264.7 mouse macrophages.
Figure 3:
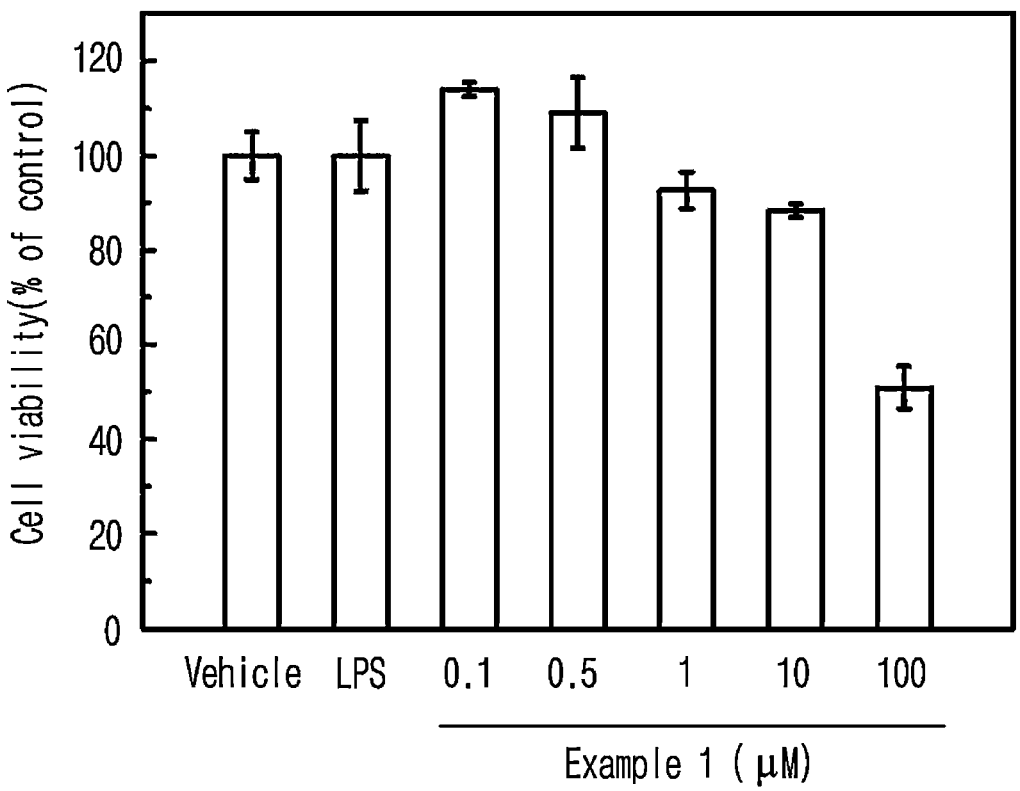

In FIG. 3, the upper graph shows the NO production rate measured by absorbance using Griess reagent as percentages compared to LPS after regulating NO production by LPS (regulating inflammatory response), and treating the compound of Example 1 of the present invention with 0.1, 0.5, 1, 10, and 100 μM, respectively, and the lower graph shows the cell viability rate according to the treatment of each LPS and the compound of Example 1 of the present invention with 0.1, 0.5, 1, 10, and 100 μM, respectively, as percentages compared to the control.

As shown in FIG. 3, it was confirmed that the NO production was inhibited by the treatment of the compound of Example 1 of the present invention, and the inhibitory effect of the NO production was increased as the treatment concentration was increased, but the compound of Example 1 of the present invention showed no significant cytotoxicity.

<2-2> Measurement of Inflammatory Response-Related Cytokine Gene Expression

In RAW264.7 macrophages activated by treatment of LPS, the expressions of inflammatory cytokine mRNA and protein are increased. Inflammatory cytokines are known to activate macrophages and mediate acute and chronic inflammatory responses. Therefore, investigating the inhibition of cytokine mRNA and protein secretion by LPS stimulation is important for the development of anti-inflammatory drugs.

Raw 264.7 mouse macrophages were aliquoted in a 96-well plate at the density of $1\times10^5$ cells/well and stabilized in a 37° C., 5% $CO_2$ incubator for 24 hours. The Raw 264.7 cells were treated with the compound of Example 1 at the concentration of 1 or 10 μM. After 1 hour, the cells were treated with 1 ug/ml of LPS and cultured for 24 hours. After removing the medium, the cells were washed with PBS. After detaching the cells using 0.1% trypsin-EDTA, the cells were collected by centrifugation. RNA was isolated from the cell precipitation using Trizole reagent. The amount of the isolated RNA was quantified by measuring absorbance at 260 nm. Real-time polymerase chain reaction was performed using a real-time PCR machine (ABI 7500 fast-real time PCR, Applied Biosystem, USA) by mixing about 100 ng of RNA with Verso SYBR Green 1-Step qRT-PCR Low ROX Mix according to the manufacturer's manual.

The genes used for real-time polymerase chain reaction were obtained from Bioneer. The polymerase reaction was carried out at 50° C. for 15 minutes and at 95° C. for 15 minutes, followed by denaturation at 95° C. for 15 seconds, annealing at 60° C. for 15 seconds, polymerization at 72° C., 40 cycles from denaturation to polymerization. The results are shown in FIG. 4.

Figure 4:
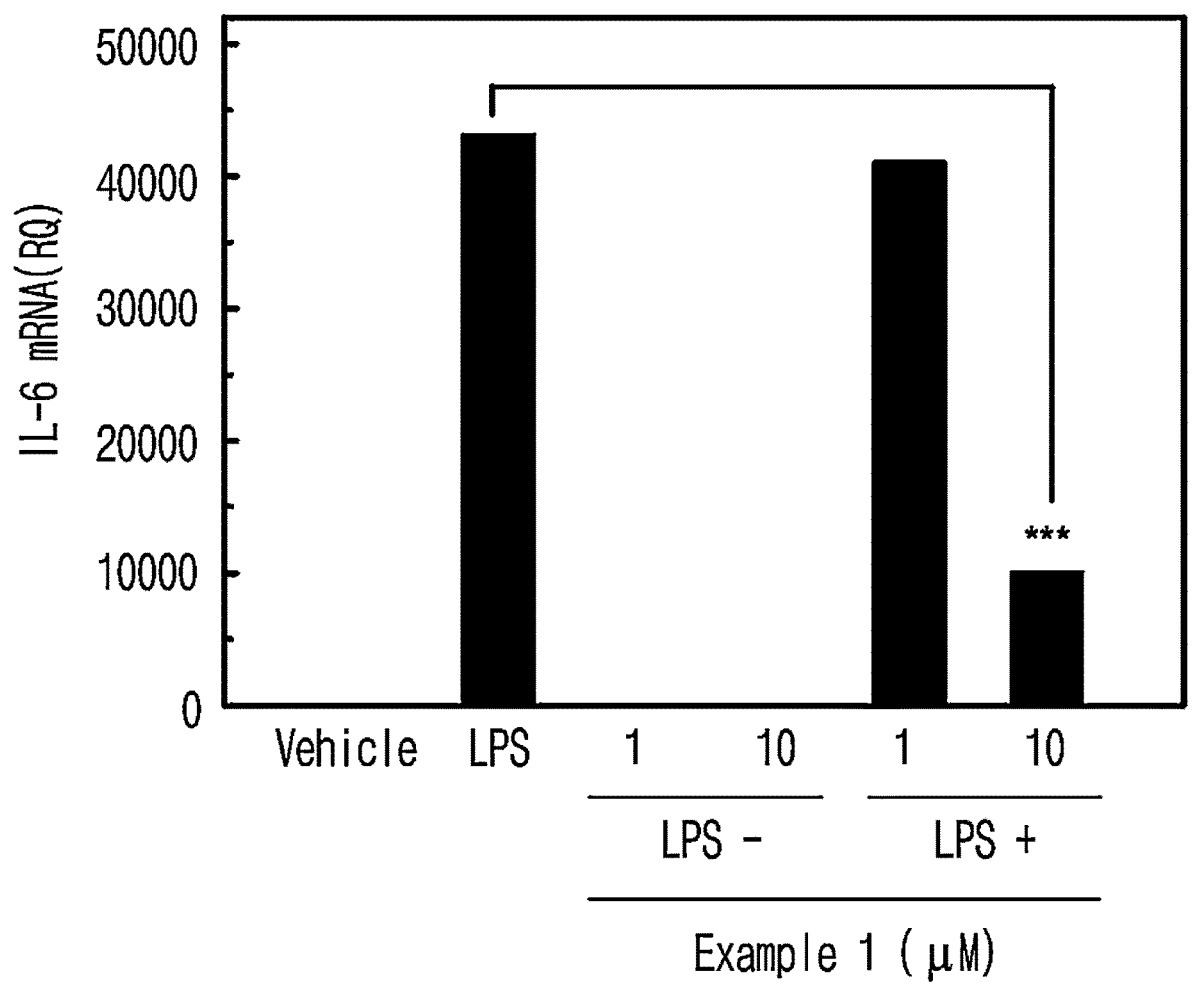
FIG. 4 is a graph illustrating the effect of the compound of Example 1 of the present invention on the expression of the inflammatory response-related cytokine IL-6 gene.

FIG. 4 is a graph illustrating the effect of the compound of Example 1 of the present invention on the expression of the inflammatory response-related cytokine IL-6 gene.

<2-3> Measurement of Inflammatory Response-Related Protein Expression

In order to measure the anti-inflammatory effect of the novel isoquinoline derivative of the present invention, an experiment was performed as follows.

In Raw 264.7 macrophages, the inflammatory proteins interleukin-6 (IL-6) and interleukin-1beta (IL-1β) were secreted out of the cells due to the regulation of inflammatory response by LPS treatment. This experiment is a method to evaluate the anti-inflammatory activity by measuring the amount of inflammatory proteins secreted after the regulation of the inflammatory response caused by LPS using an enzyme-linked immunosorbent assay (ELISA).

Particularly, Raw 264.7 mouse macrophages were aliquoted in a 96-well plate at the density of $1\times10^5$ cells/well and stabilized in a 37° C., 5% $CO_2$ incubator for 24 hours. The Raw 264.7 cells were treated with the compound of Example 1 at the concentrations of 0.1, 1 and 10 μM. After 1 hour, the cells were treated with 1 ug/ml of LPS and cultured for 24 hours. After taking only the cell culture medium, centrifugation was performed at 13,000 rpm for 5 minutes to take only the supernatant. The secreted Interleukin was quantified using a commercially available kit from Elabscience according to the manufacturer's manual. According to the method, the cell culture solution was dispensed into the provided wells (100 μl/well), and then incubated at 37° C. for 90 minutes. The culture medium was removed and 100 μl of a biotin-conjugated selective antibody was reacted at 37° C. for 1 hour, and then washed three times with a washing solution. Thereafter, 100 μl of a solution labeled with horseradish peroxidase (HRP) was reacted at 37° C. for 30 minutes, and then washed 5 times with a washing solution. After adding 90 μl of a solution containing a HRP-specific substrate, incubated at 37° C. for 15 minutes. The reaction was terminated by adding 90 μl of a termination solution, and the absorbance was measured at 450 nm. The experimental results are shown in FIG. 5.

Figure 5:
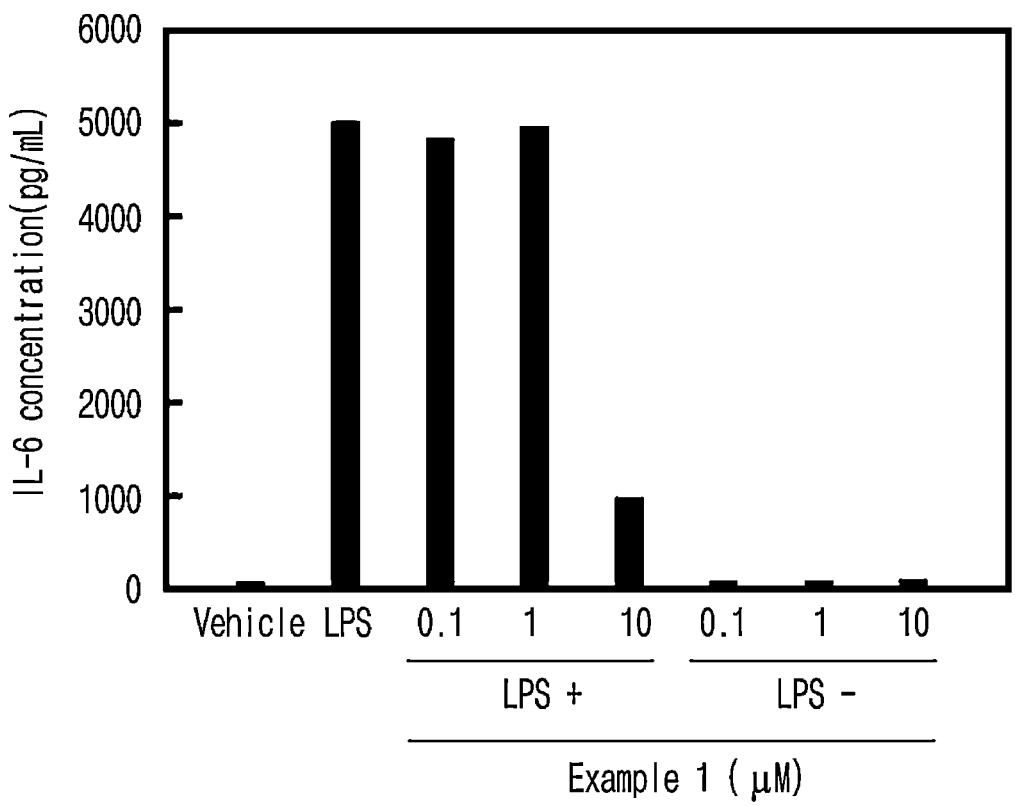
FIG. 5 is a set of graphs illustrating the effect of the compound of Example 1 of the present invention on the secretion of the inflammatory response-related proteins IL-6 and IL-1β.
Figure 5:
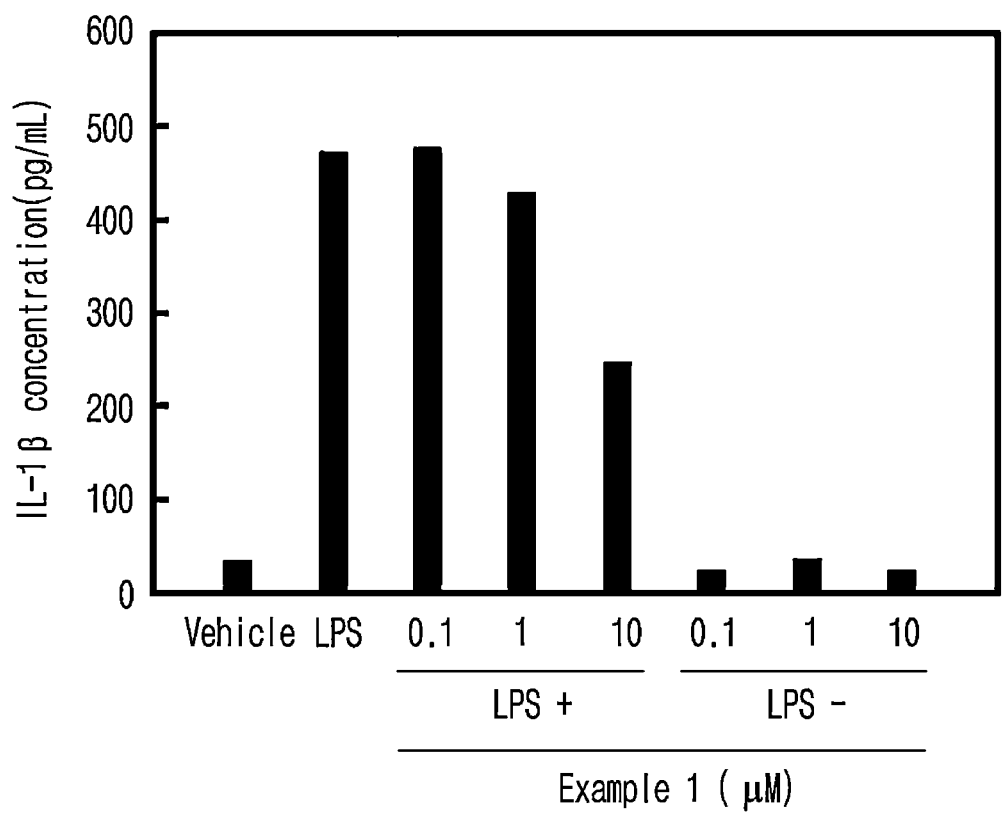

FIG. 5 is a set of graphs illustrating the effect of the compound of Example 1 of the present invention at the concentrations of 0.1, 1, and 10 μM on the secretion of the inflammatory response-related proteins IL-6 and IL-1β.

<2-4> Evaluation of Whitening Effect

In order to evaluate the whitening effect of the novel isoquinoline derivative of the present invention, an experiment was performed as follows.

Black melanocytes of zebrafish do not migrate to keratinocytes, but rather exist in melanocytes. When observing the regeneration of melanin pigment, after inhibiting the formation of melanin pigment, it can be investigated by limiting it to the melanocyte generation pathway, and it is easy to observe the melanin synthesized in the initial stage of development. Therefore, zebrafish is more useful for the study of melanin pigment changes compared to other animal models (Logan D W, Burn S F, Jackson I J. (2006) Regulation of pigmentation in zebrafish melanophores. Pigment Cell Res. 2006 June; 19(3):206-13.).

Particularly, zebrafish fertilized eggs 10 hours after fertilization were placed in a 24-well plate (10 eggs/well), and 1 ml of egg water was added to each well of the plate. The compound of Example 1 was added to each well at the concentrations of 0.1 μM and 1 μM, so that the final volume of each well was 2 ml. Then, each 24-well plate was wrapped in foil to block light, and then incubated in a 28° C. incubator for 22 hours. At 32 hours after fertilization, in order to photograph the formation of black melanocytes, the chorion of the developing embryo was peeled off using a forcep (Fine Science Tools). After anesthetizing the developing embryo with Tricaine (4 g/L), the embryo was photographed on 3% methyl cellulose. As the equipment for photographing the developing embryo, a LEICA MZ10F fluorescence microscope, a LEICA DFC425 camera, and Leica Application Suite software (v4.5) were used. In all the experimental procedures, egg water sterilized after dissolving 60 mg/L of sea salt (Sigma-Aldrich, S9883) in tertiary distilled water was used as a solution for culturing the developing embryo. As a control group, a solvent control group (0.4% DMSO) and phenylthiourea (200 μM PTU), known as a tyrosinase inhibitor, were used (FIG. 6A).

Figure 6B:
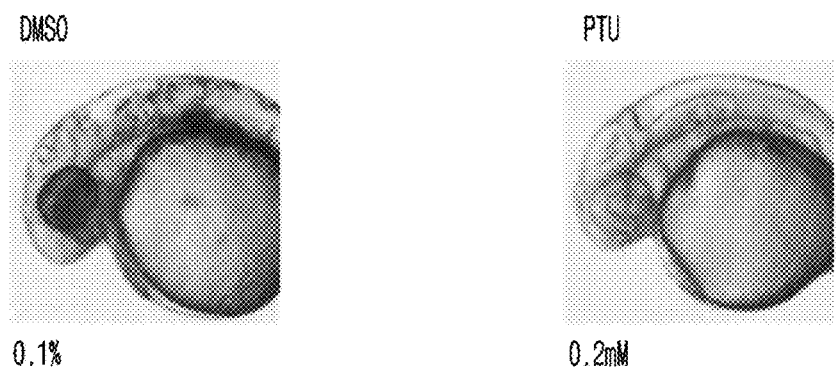
FIG. 6B is a set of zebrafish juvenile fish photographs confirming the effect of inhibiting melanocyte formation at 22 hours after the treatment of the compound of Comparative Example 1 of the present invention in fertilized zebrafish eggs 10 hours after fertilization (32 hours after fertilization).
Figure 6B:
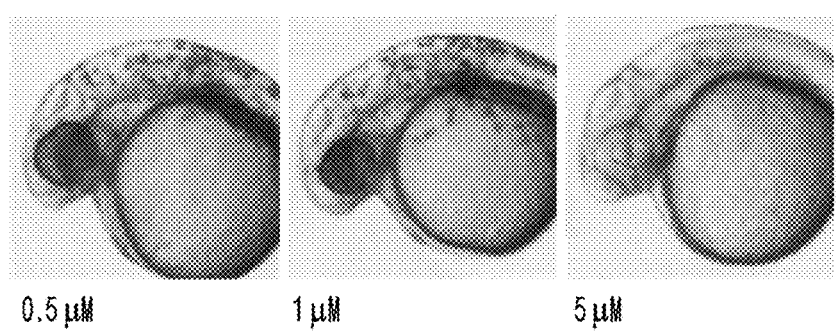
Figure 6C:
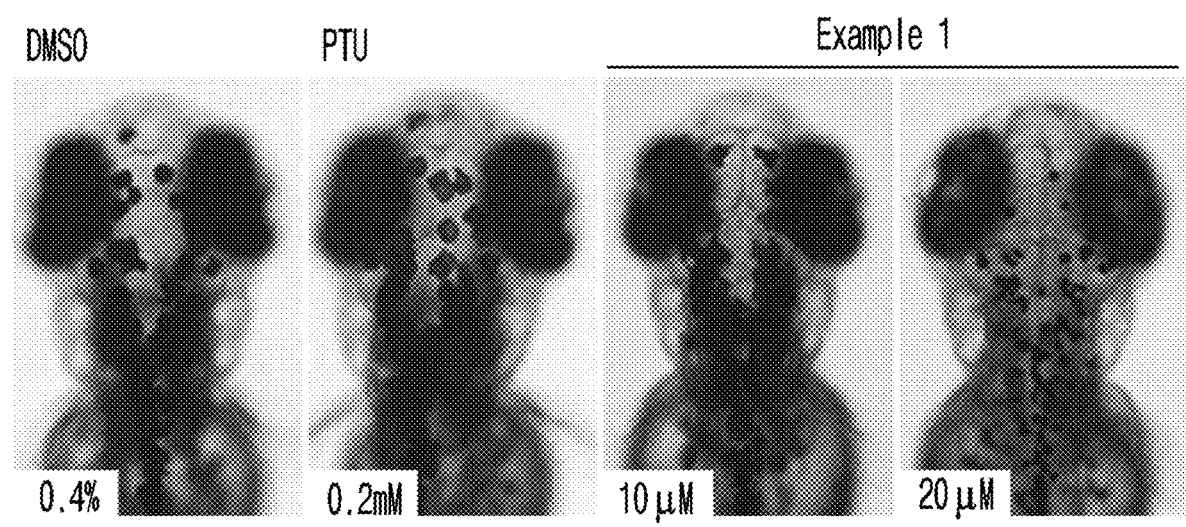
FIG. 6C is a set of zebrafish juvenile fish photographs confirming the effect of inhibiting melanocyte formation at 12 hours after the treatment of the compound of Example 1 of the present invention in fertilized zebrafish eggs 60 hours after fertilization (72 hours after fertilization).

In the same manner, experiments were performed with the compound of Comparative Example 1 at the concentrations of 0.5 μM, 1 μM, and 5 μM, and the results are shown in FIG. 6B.

On the other hand, in order to confirm the ability of the compound of the present invention to inhibit the melanin synthesis of the already generated melanocytes, the following experiment was performed with juvenile fish 60 hours after fertilization. Particularly, juvenile fish 60 hours after fertilization were placed in a 24-well plate (10/well), and 1 ml of egg water was added to each well of the plate. The compound of Example 1 was added to each well at the concentrations of 10 μM and 20 μM, so that the final volume of each well was 2 ml. Then, each 24-well plate was wrapped in foil to block light, and then incubated in a 28° C. incubator for 12 hours. In order to photograph the formation of black melanocytes, the developing embryo was anesthetized with Tricaine (4 g/L), and then the embryo was photographed on 3% methyl cellulose. The above-mentioned equipment was used for photographing (FIG. 6C).

The excellent melanin synthesis inhibitory effect of the novel isoquinoline derivative of the present invention was confirmed. In particular, at 32 hours after fertilization, the synthesis of melanin was inhibited in the group treated with the compound of Example 1 of the present invention at the concentration of 1 μM at a level similar to that in the group treated with PTU. This means that the compound of Example 1 has a 5-fold or more superior activity, compared to the compound of Comparative Example 1 that inhibited the synthesis of melanin at a level similar to that of the PTU-treated group when treated with 5 μM. In addition, at 72 hours after fertilization, compared to the group treated with PTU at the concentration of 0.2 mM, the compound of Example 1 of the present invention was confirmed to have a superior melanin synthesis inhibitory effect compared to PTU, especially when treated with 20 μM.

<2-5> Evaluation of Fatty Liver Inhibitory Effect

In order to evaluate the inhibitory efficacy of the novel isoquinoline derivative of the present invention on fatty liver, an experiment was performed as follows using Lipid-Green2 staining reagent capable of staining lipid droplets.

The proportion of fat in the normal liver is about 5%, and if more fat is accumulated than this, it is called fatty liver. Fatty liver is largely divided into alcoholic fatty liver caused by excessive drinking and non-alcoholic fatty liver caused by obesity, diabetes, hyperlipidemia, drugs, and the like. The main causes of fatty liver are drinking and obesity. Diseases such as hyperlipidemia with a high blood lipid concentration or diabetes may appear together with fatty liver. Drugs such as corticosteroids (steroids) or female hormones can also cause fatty liver.

Tamoxifen is a nonsteroidal anti-estrogen agent that binds to estrogen receptor α/β by competing with estrogen. It was developed by ICI (UK) and has been used the most as an endocrine therapy for female hormone-dependent cancer since the 1980s. In particular, it is known that hepatocyte necrosis occurs in the zebrafish juvenile fish treated with tamoxifen, and steatosis is known to appear in the adult liver.

Particularly, the zebrafish used in this Experimental Example were juvenile fish 5 days after fertilization. Healthy juvenile fish were placed in a 24-well plate (10/well), and 1 ml of egg water was added to each well of the plate. As a negative control that could not regulate fatty liver, DMSO diluted at 0.4% was exposed to juvenile fish, and tamoxifen (Sigma-Aldrich, T5648) diluted at 5 µM was exposed to juvenile fish to control alcoholic fatty liver. In order to investigate the fatty liver inhibitory efficacy of the compound of Example 1 of the present invention, the compound (0.5 µM, 1 µM and 5 µM) was mixed with 5 µM tamoxifen and exposed to juvenile fish (final volume of each well: 2 ml). The 24-well plate containing the compound was wrapped in foil to block light, and then incubated in a 28° C. incubator for 22 hours. The plate was washed with egg water 3 times for 5 minutes to remove the compound from each well. For fat-specific staining, LipidGreen2 diluted at 5 µM was exposed to juvenile fish for 30 minutes, and then washed 3 times with egg water for 5 minutes. To evaluate the fatty liver of zebrafish juvenile fish, the developing embryo was anesthetized with Tricaine (4 g/L), and then photographed on 3% methyl cellulose. As the equipment for photographing the developing embryo, a LEICA MZ10F fluorescence microscope, a LEICA DFC425 camera, and Leica Application Suite software (v4.5) were used. For the fluorescence wavelength, a GFP Plants filter set (Excitation 470/40 nm, Emission 525/50 nm) was used. To quantify the liver area and the degree of fat staining of juvenile fish on the image, the area and the fluorescence intensity of the liver part of each image were quantified using ImageJ 1.50i software (National Institutes of Health, USA) and converted into heatmap images. The experimental results are shown in FIGS. 7 and 8.

Figure 7:
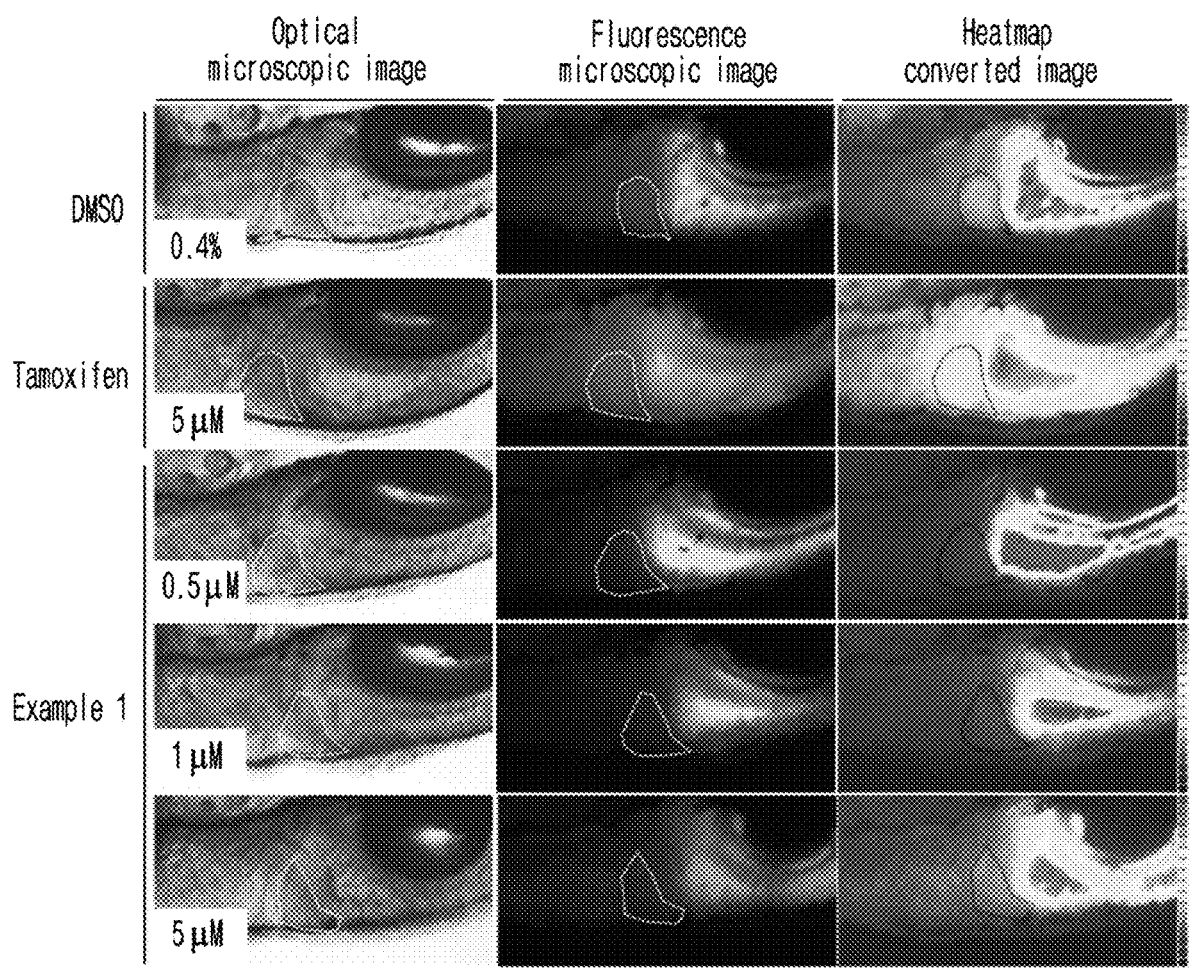
FIG. 7 is a set of general microscope images, fluorescence microscope images and heatmap conversion images observed after the treatment of DMSO, tamoxifen and the compound of Example 1 of the present invention in zebrafish juvenile fish 5 days after fertilization.

FIG. 7 is a set of general microscope images, fluorescence microscope images and heatmap conversion images observed after the treatment of DMSO, tamoxifen and the compound of Example 1 of the present invention in zebrafish juvenile fish 5 days after fertilization.

Figure 8:
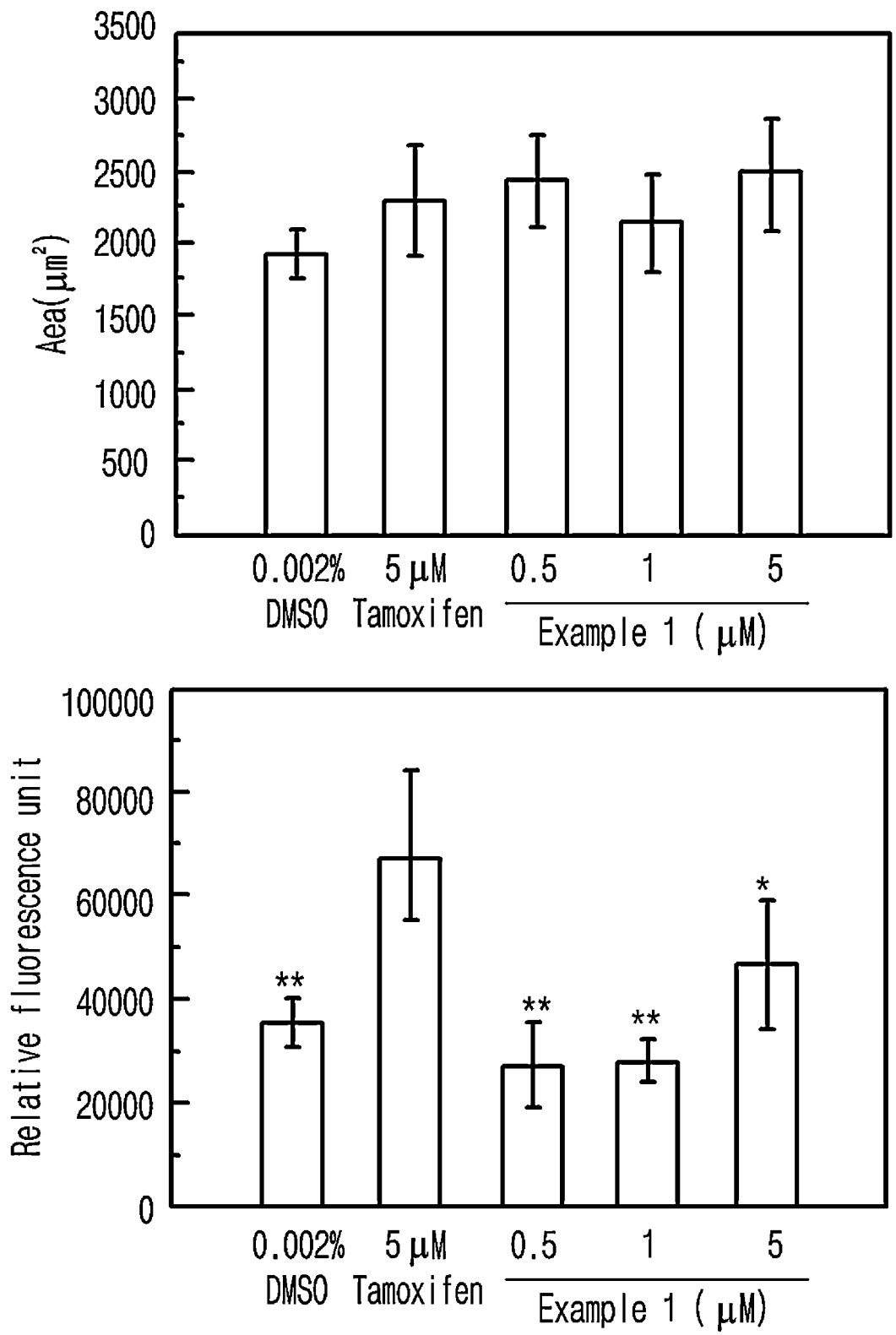
FIG. 8 is a set of graphs illustrating the results of quantification of liver area (top) and fluorescence intensity (bottom) on the zebrafish juvenile fish images observed after the treatment of DMSO, tamoxifen and the compound of Example 1 of the present invention in zebrafish juvenile fish 5 days after fertilization using ImageJ 1.50i softwear (National Institutes of Health, USA) (The p values are the t-test results for each experimental group compared to the tamoxifen-treated group. *p 0.01, **p≤0.001).

FIG. 8 is a set of graphs illustrating the results of quantification of liver area (top) and fluorescence intensity (bottom) on the zebrafish juvenile fish images observed after the treatment of DMSO, tamoxifen and the compound of Example 1 of the present invention in zebrafish juvenile fish 5 days after fertilization using ImageJ 1.50i softwear (National Institutes of Health, USA) (The p values are the t-test results for each experimental group compared to the tamoxifen-treated group. *$p \leq 0.01$, **$p \leq 0.001$).

In FIG. 7, the white dotted lines on the general microscope image and the fluorescence microscope image and the black dotted line on the heatmap conversion image indicate the liver part of the same juvenile fish. In particular, in the heatmap conversion image, a red color indicates the strong fluorescence intensity, and a blue color indicates the weak fluorescence intensity.

As shown in FIG. 7, as a result of LipidGreen2 fat staining, it was confirmed that the fatty liver regulated by tamoxifen was restored to the normal level in the group treated with the compound of Example 1 of the present invention.

In FIG. 8, the upper part is a graph statistically confirming that the liver area of the juvenile fish of the group treated with the compound of Example 1 of the present invention or tamoxifen was maintained at the liver area level of normal juvenile fish, and the lower part is a graph confirming that the fluorescence intensity of the juvenile fish of the group treated with the compound of Example 1 of the present invention was decreased to the normal level compared to the fluorescence intensity of the juvenile fish of the group treated with tamoxifen. From the above results, it was confirmed that the compound of Example 1 can be effectively used for the treatment or amelioration of fatty liver.

<Experimental Example 3> Toxicity Test

<3-1> Non-Selective General Cytotoxicity Test

In order to evaluate the non-selective cytotoxicity of the compound of Example 1 of the present invention in various cell lines, the following experiment was performed.

In this experiment, the cell lines derived from different species, VERO (African green monkey kidney cell line), HFL-1 (human embryonic lung cell line), L929 (mouse fibroblast cell line), NIH 3T3 (mouse embryonic fibroblast cell line), CHO-K1 (Chinese hamster ovary cell line) and HMV-II (human malignant melanoma cell line), were used.

Particularly, VERO, HFL-1, L929 and NIH 3T3 cell lines were cultured in DMEM, CHO-K1 was cultured in RPMI1640 medium, and HMV-II was cultured in DME/F-12 medium. 10% FBS (Fetal Bovine Serum) and 100 µg/mL of antibiotics were added to each medium. The cells were acclimatized and cultured in a humidified 37° C. 5% $CO_2$ incubator, washed with PBS (phosphate buffer solution) at the time of growth that occupies 70-80% of the culture dish every 2-3 days, and then subcultured by treating with Trypsin-EDTA (Gibco, USA).

The cells used in this Experimental Example were aliquoted into a 96-well culture plate at the density of 15,000-25,000 cells/well, and then acclimatized and cultured in a humidified 37° C. 5% $CO_2$ incubator for 24 hours. The compound of Example 1 of the present invention was prepared to be 10 mM using DMSO, and diluted sequentially. Each cell line was treated with the compound at the final concentration, and cultured for 24 hours. The cell viability was measured according to the standard method using a Cyto XTM cell viability assay kit (LPS solution). 10 µl of a chromogenic reagent was added to each well and incubated for 2 hours in a humidified 37° C. 5% $CO_2$ incubator, followed by measuring the absorbance at 450 nm. The survival rate was measured by calculating the ratio of the absorbance changed compared to the absorbance measured in the group treated with DMSO alone. The results are shown in FIG. 9.

Figure 9:
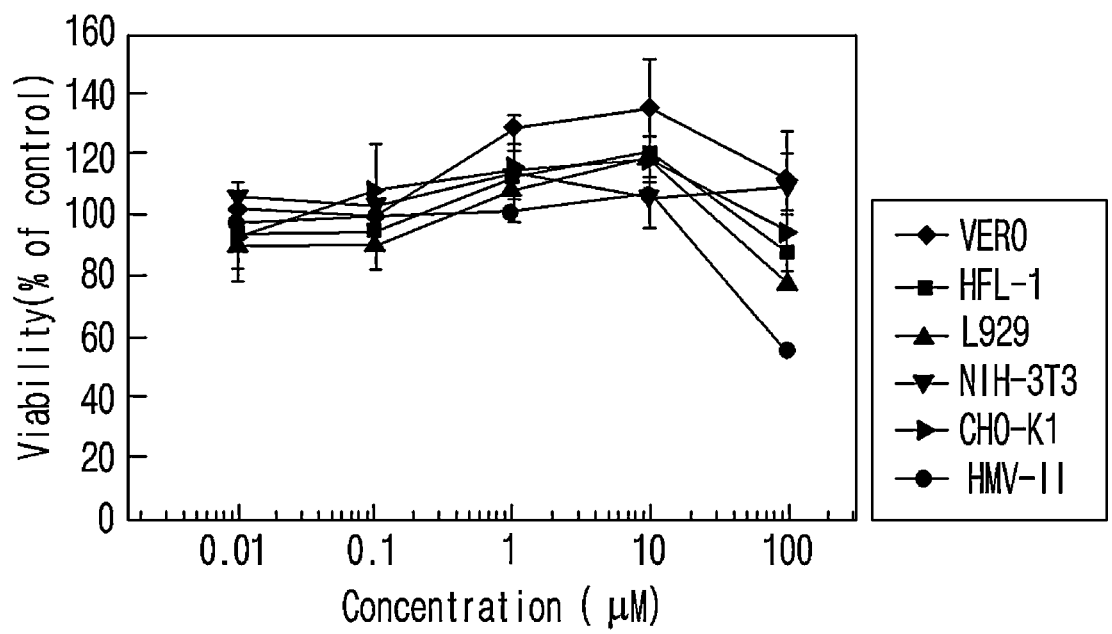
FIG. 9 is a graph illustrating the cell viability of VERO, HFL-1, L929, NIH 3T3, CHO-K1 and HMV-II cell lines according to the concentration of the compound of Example 1 of the present invention treated.

FIG. 9 is a graph illustrating the cell viability of VERO, HFL-1, L929, NIH 3T3, CHO-K1 and HMV-II cell lines according to the concentration of the compound of Example 1 of the present invention treated.

As shown in FIG. 9, the compound of Example 1 of the present invention had no significant toxicity in all cell lines up to 10 µM, and showed less than 50% cytotoxicity at the maximum test concentration of 100 µM.

<3-2> Cardiotoxicity Test

In order to evaluate the possibility of inducing cardiotoxicity of the compound of Example 1 of the present invention in vivo, the inhibitory potential to the hERG (human ether-a-go-go related gene) $K^+$ channel protein, known as a main cause of arrhythmias, was tested.

First, a ligand binding test was performed to evaluate the binding force of the compound of Example 1 binding to the hERG channel protein in vitro. A biological membrane containing the hERG channel protein was aliquoted in a 384-black well plate (10 μl/well) at room temperature, and DMSO, E-4031 (positive control), and the compound of Example 1 prepared to be 4 times the final test concentration were added thereto (5 μl/well). A tracer material with a fluorescent material attached to astemizole, known as a selective binding substance to the hERG channel protein, was dispensed into a mixture of the two solutions (5 μl/well), and then incubated for 2 hours at room temperature where light was blocked. In order to excite the tracer material included in the reaction solution, the light of 530 nm was irradiated and the light of 585 nm returned back was measured by the polarization method. In this experiment, the high polarization value by the tracer material means a lot of binding between the hERG protein and the tracer. Conversely, the low polarization value indicates a lot of binding between the hERG protein and the test material. The binding force of the test material to the hERG protein was expressed as the inhibition rate (%) compared to the group treated with DMSO.

Next, in order to evaluate the activity of the hERG channel protein using an electrophysiological method, a patch clamp test was performed. The activity of the hERG channel protein was measured using the HEK-293 cell line overexpressing the hERG channel protein. The cells were acclimatized and cultured in a humidified 37° C. 5% $CO_2$ incubator, washed with PBS (phosphate buffer solution) at the time of growth that occupies 70-80% of the culture dish every 2-3 days, and then subcultured by treating with Trypsin-EDTA. For the test, $2 \times 10^5$ cells were aliquoted in a 60 mm cell culture dish, and then cultured in a humidified 5% $CO_2$ incubator for 48 hours. The cultured cells were detached by treating Trypsin-EDTA (Gibco, USA), and the flow of $K^+$ by the hERG channel protein was measured by applying an automated patch clamp equipment (PatchXpress, Molecular Device).

Figure 10:
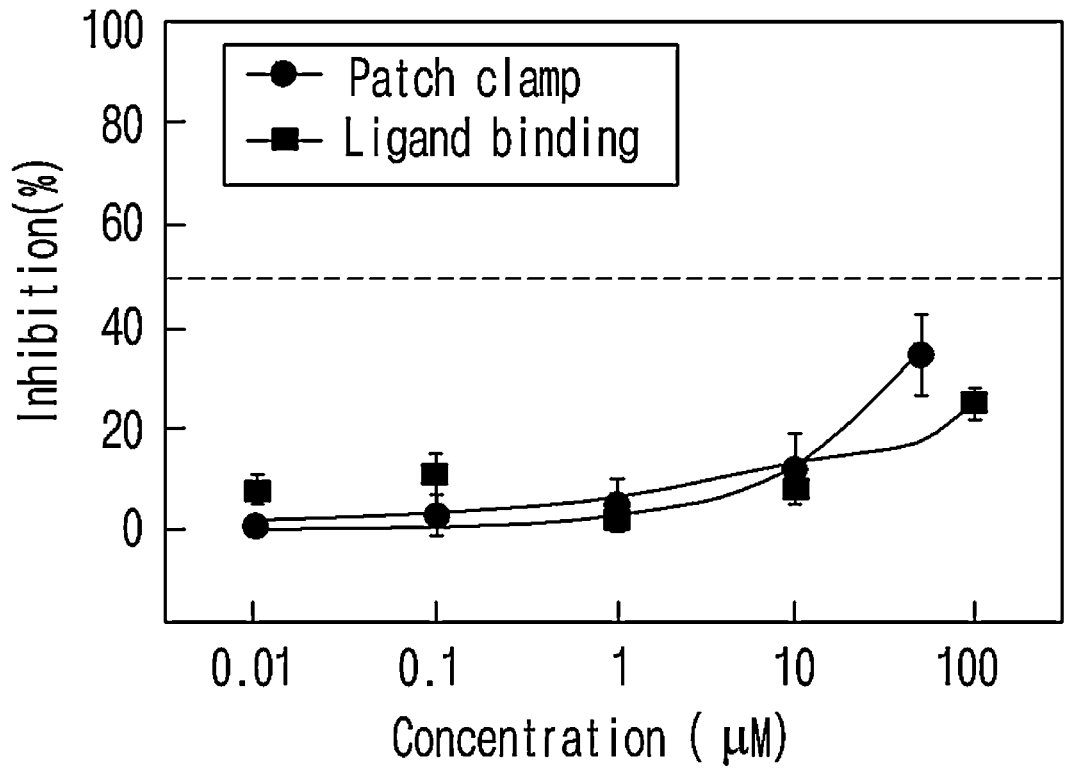
FIG. 10 is a graph illustrating the inhibition of the binding and ion channel opening activity of the hERG channel protein by the compound of Example 1 of the present invention, measured by a ligand binding assay and an electrophysiology experiment, respectively.

The experimental results of the two experiments above are shown in FIG. 10.

FIG. 10 is a graph illustrating the inhibition of the binding and activity of the hERG channel protein by the compound of Example 1 of the present invention, presented by ligand binding and patch clamp curves, respectively.

As shown in FIG. 10, the inhibition of the binding and activity of the hERG channel protein by the compound of Example 1 of the present invention was found to be about 10% at 10 μM. These results are significantly less than the 50% inhibition rate at 10 μM, which is a standard for judging general toxicity, and thus, it is determined that the compound of Example 1 of the present invention has a low possibility of inducing cardiotoxicity by inhibiting the hERG channel protein in vivo.

<3-3> Skin Toxicity Test

In order to evaluate the skin toxicity that may be induced upon skin contact of the compound of Example 1 of the present invention, the following experiment was performed using the artificial skin prepared with a structure similar to the skin of a living body.

Particularly, the experiment was performed according to OECD Guideline for the Testing of Chemicals No. 439, OECD (2010) and the method recommended by the manufacturer (Tegoscience).

First, the artificial skin cultured in agarose medium was transferred to a 12-well cell culture plate, to which culture medium was added, followed by culture in a humidified 37° C. 5% $CO_2$ incubator for one day. The medium on the artificial skin culture surface was eliminated, and 90 μl of the compound of Example 1 of the present invention diluted with PBS was evenly applied to the skin surface, followed by incubation at room temperature for 15 minutes. The cell surface was washed twice with 10 ml of PBS, and a fresh culture medium was added, followed by incubation in a humidified 37° C. 5% $CO_2$ incubator for 42 hours. In order to measure the viability of the skin, the artificial skin was transferred to a 12-well plate containing 2 ml of MTT solution (0.3 mg/ml), followed by culture for 3 hours. The stained artificial skin tissue was taken and transferred to a tube containing 500 μl of 0.04 N-isopropanol, and then incubated with shaking for 4 hours to decolorize. The solution was centrifuged at 13,000 rpm for 5 minutes, 100 μl of the supernatant was transferred to each well of a 96-well plate, and absorbance was measured at 570 nm. The results are shown in FIG. 11.

Figure 11:
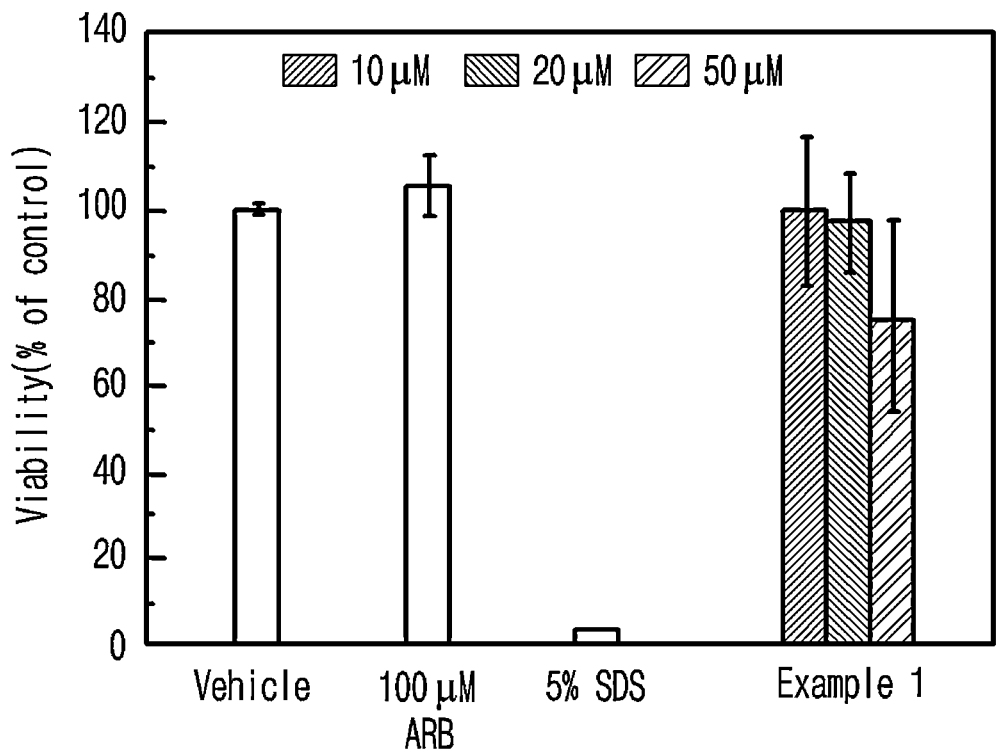
FIG. 11 is a graph illustrating the survival rate of the groups treated with a vehicle, ARB, SDS, and 10, 20 and 50 μM of the compound of Example 1 of the present invention, calculated based on the absorbance measured after eluting MTT stained on the artificial skin tissue using isopropanol.

FIG. 11 is a graph illustrating the survival rate of the groups treated with a vehicle, ARB, SDS, and 10, 20 and 50 μM of the compound of Example 1 of the present invention, calculated based on the absorbance measured after eluting MTT stained on the artificial skin tissue using isopropanol.

As shown in FIG. 11, a significant decrease of the MTT color development due to necrosis of the skin tissue was observed in the control group treated with 5% SDS, whereas in the group treated with the compound of Example 1 of the present invention, there was no significant decrease of the survival rate up to 20 μM, and a slight decrease of the survival rate was confirmed only in the group treated with the compound at the concentration of 50 μM, the maximum concentration.

<3-4> Ocular Toxicity Test

In order to evaluate the ocular toxicity that may be induced upon ocular exposure of the compound of Example 1 of the present invention, the following experiment was performed using the cultured artificial cornea.

The artificial corneal tissue cultured in agarose medium was transferred to a 12-well cell culture plate, to which culture medium was added, followed by culture in a humidified 37° C. 5% $CO_2$ incubator for one day. The medium on the artificial cornea culture surface was eliminated, and 30 μl of the compound of Example 1 of the present invention diluted with PBS was evenly applied to the cornea surface, followed by incubation at room temperature for 30 minutes. The cell surface was washed twice with 10 ml of PBS, and a fresh culture medium was added, followed by incubation in a humidified 37° C. 5% $CO_2$ incubator for 30 minutes. In order to measure the viability of the cornea, the artificial cornea was transferred to a 12-well plate containing 2 ml of MTT solution (1 mg/ml), followed by culture for 3 hours. The stained artificial corneal tissue was taken and transferred to a tube containing 1.5 ml of isopropanol, and then incubated with shaking to decolorize. The solution was centrifuged at 13,000 rpm for 5 minutes, 100 μl of the supernatant was transferred to each well of a 96-well plate, and absorbance was measured at 570 nm. The results are shown in FIG. 12.

Figure 12:
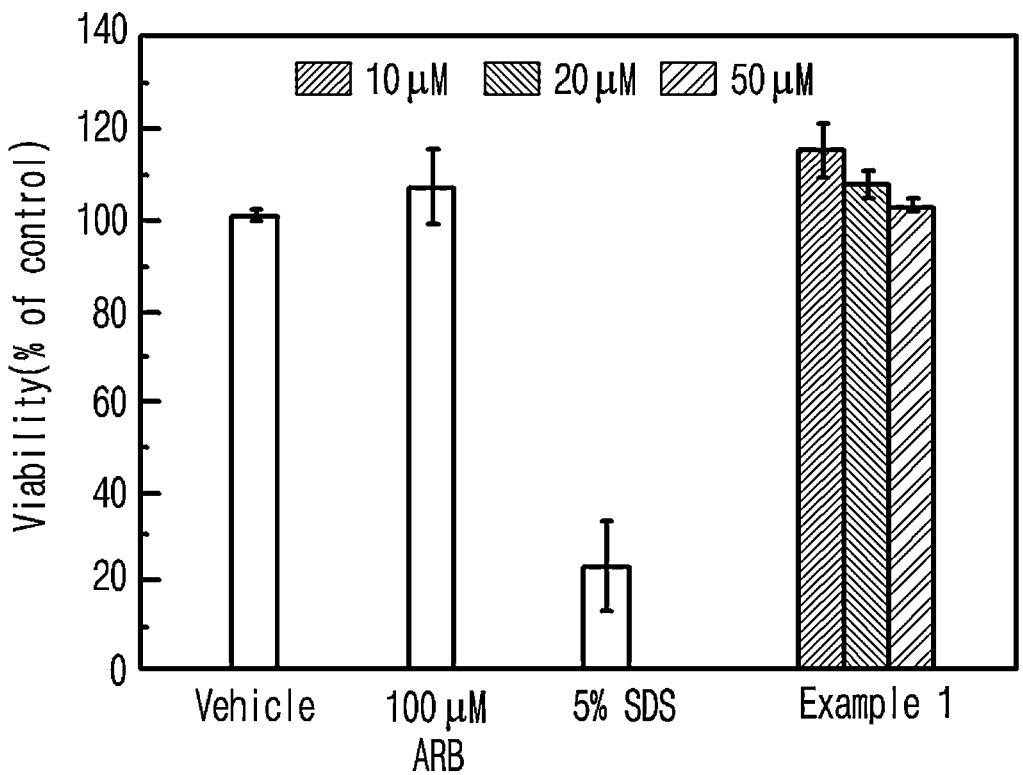
FIG. 12 is a graph illustrating the survival rate of the groups treated with a vehicle, ARB, acetic acid, and 10, 20 and 50 μM of the compound of Example 1 of the present invention, calculated based on the absorbance measured after eluting MTT stained on the artificial corneal tissue using isopropanol.

FIG. 12 is a graph illustrating the survival rate of the groups treated with a vehicle, ARB, acetic acid, and 10, 20 and 50 μM of the compound of Example 1 of the present invention, calculated based on the absorbance measured after eluting MTT stained on the artificial corneal tissue using isopropanol.

As shown in FIG. 12, a significant decrease of the MTT color development due to necrosis of the corneal tissue was observed in the control group treated with 10% acetic acid, whereas in the group treated with the compound of Example 1 of the present invention, there was no significant decrease of the survival rate up to 50 μM, the maximum concentration.

<3-5> Evaluation of ALT (Aminotransferase) Activity, a Liver Damage Index

In order to evaluate the effect of the compound of Example 1 of the present invention on the activity of a liver damage index, the activity of ALT (aminotransferase), a liver damage index, was analyzed in ob/ob mice, an obesity-controlled rodent model.

ALT is alanine aminotransferase, which is an enzyme that helps amino acid exchange between keto acids and amino acids. When the enzyme leaked into the blood during cell damage is measured, the enzyme is elevated in liver damage such as viral hepatitis.

Particularly, ob/ob mice (leptin deficient C57B/6 mice) were used as experimental animals, and 10 mpk or 100 mpk of the compound of Example 1 of the present invention was administered for 3 weeks. After administration of the compound, the animals were stunned with $CO_2$ gas and the livers were collected. After washing the liver tissues with saline, 50 mg was taken and homogenized. Only the lysate was collected separately by centrifugation. The lysate and the substrate for enzyme reaction were added thereto, and the fluorescence value was measured at 535/587 nm. The results are shown in the graph of FIG. 13.

Figure 13:
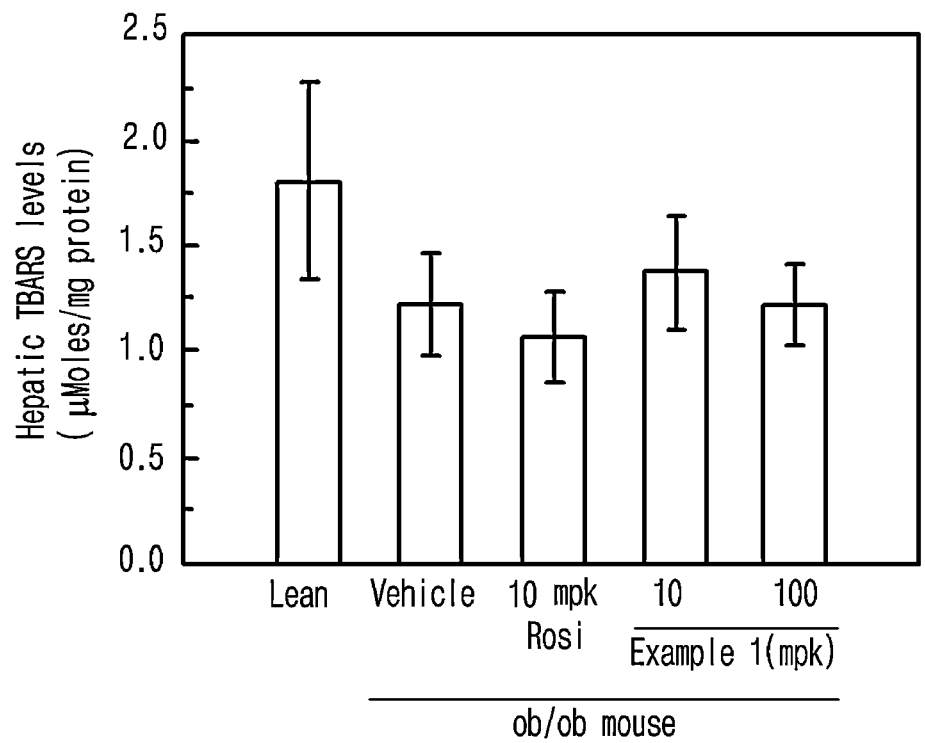
FIG. 13 is a graph illustrating the ALT (aminotransferase) activity, a liver damage index, measured after the administration of a vehicle, a positive control (10 mpk Rosi), and the compound of Example 1 of the present invention (10 mpk and 100 mpk), respectively, in an obesity-controlled rodent model.

FIG. 13 is a graph illustrating the ALT (aminotransferase) activity, a liver damage index, measured after the administration of a vehicle, a positive control (10 mpk Rosi), and the compound of Example 1 of the present invention (10 mpk and 100 mpk), respectively, in an obesity-controlled rodent model.

<3-6> Evaluation of Oxidative Stress

In order to evaluate the oxidative stress of the compound of Example 1 of the present invention, the activity of TBARS (Thiobarbituric acid reactive substance), an oxidative stress index, was analyzed in ob/ob mice, an obesity-controlled rodent model.

Lipid peroxidation is a well-known mechanism of cell damage and is used as an index of oxidative stress. Measurement of TBARS is a method for confirming lipid peroxidation, in which the degree of lipid peroxidation can be confirmed by measuring that MDA and TBA (thiobarbituric acid) combine to form an MDA-TBA product.

Particularly, ob/ob mice (leptin deficient C57B/6 mice) were used as experimental animals, and 10 mpk or 100 mpk of the compound of Example 1 of the present invention was administered for 3 weeks. After administration of the compound, the animals were stunned with $CO_2$ gas and the livers were collected. After washing the liver tissues with saline, 50 mg was taken and homogenized. Only the lysate was collected separately by centrifugation. The MDA-TBA product formed as a result of the reaction of MDA and TBA under the acidic condition at 95° C. was measured with $OD_{532}$. The results are shown in FIG. 14.

Figure 14:
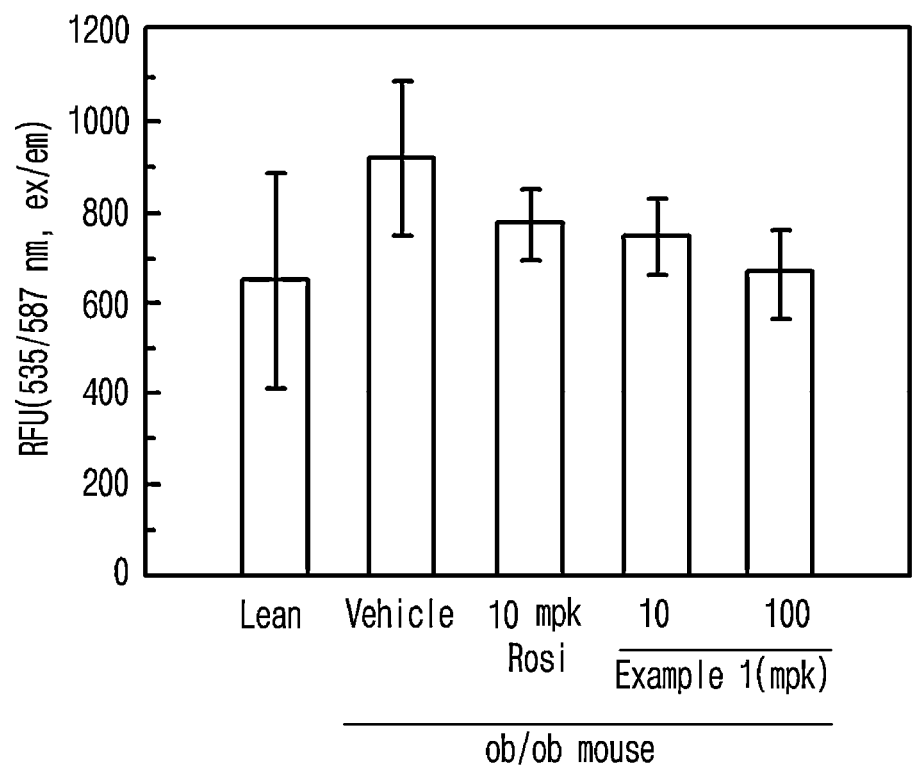
FIG. 14 is a graph illustrating the TBARS (thiobarbituric acid reactive substance) activity, an oxidative stress index, measured after the administration of a vehicle, a positive control (10 mpk Rosi), and the compound of Example 1 of the present invention (10 mpk and 100 mpk), respectively, in an obesity-controlled rodent model.

FIG. 14 is a graph illustrating the TBARS (Thiobarbituric acid reactive substance) activity, an oxidative stress index, measured after the administration of a vehicle, a positive control (10 mpk Rosi), and the compound of Example 1 of the present invention (10 mpk and 100 mpk), respectively, in an obesity-controlled rodent model.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

What is claimed is:

1. A compound represented by formula 1 below or a pharmaceutically acceptable salt thereof:

[Formula 1]

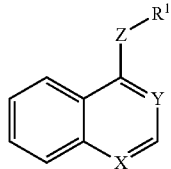

(In formula 1,

R¹ is nonsubstituted or substituted phenyl,
wherein the substituted phenyl is substituted with one or more substituents selected from the group consisting of halogen and CF3;
any one of X and Y is CH, and the other is N; and
Z is S(O)).

2. The compound or the pharmaceutically acceptable salt thereof according to claim 1, wherein the X is CH and the Y is N.

3. The compound or the pharmaceutically acceptable salt thereof according to claim 1, wherein the compound represented by formula 1 is any one selected from the group consisting of the following compounds:

1-((4-fluorophenyl)sulfinyl)isoquinoline;
4-((4-fluorophenyl)sulfinyl)quinoline;
1-((2,4-difluorophenyl)sulfinyl)isoquinoline;
1-((4-chlorophenyl)sulfinyl)isoquinoline; and
1-((4-(trifluoromethyl)phenyl)sulfinyl)isoquinoline.

4. A method for inhibiting or treating inflammatory disease by administering an effective amount of the compound or the pharmaceutically acceptable salt thereof of claim 1 to a subject in need thereof, wherein the inflammatory disease is selected from the group consisting of inflammatory bowel disease, ulcerative colitis, Crohn's disease, arthritis, dermatitis, atopic dermatitis, hepatitis, and non-alcoholic hepatitis.

5. A method for inhibiting or treating fatty liver by administering an effective amount of the compound or the pharmaceutically acceptable salt thereof of claim 1 to a subject in need thereof.

6. A method for treating skin hyperpigmentation disease by administering an effective amount of the compound or the pharmaceutically acceptable salt thereof of claim 1 to a subject in need thereof.

7. The method according to claim 6, wherein the disease is a skin disease caused by melanin overproduction.

8. A method for inhibiting melanogenesis in a certain area of a subject by administering an effective amount of the compound or the pharmaceutically acceptable salt thereof of claim 1 to a subject in need thereof.

9. The method according to claim 8, wherein the certain area is skin, hair or eye.

* * * * *